US006660483B1

(12) United States Patent
Kask et al.

(10) Patent No.: US 6,660,483 B1
(45) Date of Patent: Dec. 9, 2003

(54) DIAGNOSTIC MARKER FOR NEUROLOGICAL CONDITIONS

(75) Inventors: Kalev Kask, San Mateo, CA (US); Thorsten Melcher, San Francisco, CA (US); Daniel J. Chin, Foster City, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 261 days.

(21) Appl. No.: 09/688,078

(22) Filed: Oct. 13, 2000

Related U.S. Application Data

(60) Provisional application No. 60/159,622, filed on Oct. 14, 1999.

(51) Int. Cl.[7] .......................... C12Q 1/00; G01N 33/53; G01N 33/573

(52) U.S. Cl. ............................................ 435/7.1; 435/4

(58) Field of Search ....................................... 435/4, 7.1

(56) References Cited

PUBLICATIONS

Nakashima et al. *J. Cerebral Blood Flow and Metab., vol. 13*, pp. 255–259, 1993.*
Singer, et al., (1997), *Annu. Rev. Biochem.*, 66:475–509.
Genbank accession No. AB029015 (1999).
Genbank accession No. AW408450 (2000).
Genbank accession No. AA277075 (1997).
Genbank accession No. AA772973 (1998).
Genbank accession No. AW493796 (2000).
Genbank accession No. AW500653 (2000).
Genbank accession No. BE655266 (2000).
Genbank accession No. AA690679 (1997).
Genbank accession No. AL024179 (1999).
Genbank accession No. AW478640 (2000).
Genbank accession No. T78839 (1995).
Genbank accession No. AW428387 (2000).
Genbank accession No. AW466123 (2000).
Kanematsu et al., (1996), *Biochem. J.* 1(313):319–325.
Takeuchi et al., (1999), *Chem. Phys. Lipids*, 98:35–47.
Yagisawa et al., (1994), *J. Biol. Chem.*, 269(31):20179–20188.
Hirata et al., (1994), *Biochem. Biophys. Res. Commun.*, 205(3):1563–1571.
Kanematsu et al., (2000), *Eur. J. Biohcem.*, 267:2731–2737.
Matsuda et al., (1998), *Neurosci. Lett.*, 257:97–100.
Kanematsu et al., (1992), *J. Biol. Chem.*, 267(10):6518–6525.
Lemmon et al., (1995), *Proc. Natl. Acad. USA*, 92:10472–10476.
Otsuki et al., (1999), *Biochem. Biophys. Res. Commun.*, 266:97–193.

* cited by examiner

*Primary Examiner*—Gary Kunz
*Assistant Examiner*—Stephen Gucker
(74) *Attorney, Agent, or Firm*—Rebecca D. Taylor; Pamela J. Sherwood; Bozicevic, Field & Francis LLP

(57) ABSTRACT

The invention relates to a human phospholipase C expressed in the brain (B-PLC) and induced in response to ischemic brain tissue. The inventions provides methods and reagents useful for diagnosis and treatment of hypoxic-ischemic brain insult such as stroke.

6 Claims, 11 Drawing Sheets

FIG. 1A

```
1/1                                         31/11
ATG CCA ACA GAG AAG AAG ATC AGC AGT GCA AGT GAT TGT ATT AAT TCA ATG GTT GAG GGT
M   P   T   E   K   K   I   S   S   A   S   D   C   I   N   S   M   V   E   G
61/21                                       91/31
TCA GAA CTC AAA AAG GTT CGC TCC AAC TCT AGA ATT TAT CAT AGG TAC TTT CTA CTG GAT
S   E   L   K   K   V   R   S   N   S   R   I   Y   H   R   Y   F   L   L   D
121/41                                      151/51
GCT GAC ATG CAG AGC CTA AGG TGG GAG CCA TCT AAG AAG GAT TCT GAG AAA GCC AAG ATT
A   D   M   Q   S   L   R   W   E   P   S   K   K   D   S   E   K   A   K   I
181/61                                      211/71
GAC ATT AAA TCC ATC AAG GAA GTG AGA ACG GGA AAA AAC ACA GAC ATA TTC CGC AGC AAT
D   I   K   S   I   K   E   V   R   T   G   K   N   T   D   I   F   R   S   N
241/81                                      271/91
GGC ATT TCT GAC CAG ATA TCT GAA GAT TGT GCG TTT TCC GTC ATA TAT GGA GAG AAT TAT
G   I   S   D   Q   I   S   E   D   C   A   F   S   V   I   Y   G   E   N   Y
301/101                                     331/111
GAG TCA CTG GAT TTG GTT GCC ACT CTC GCA GAT GTT GCA AAC ATC TGG GTT ACA GGA CTG
E   S   L   D   L   V   A   T   L   A   D   V   A   N   I   W   V   T   G   L
361/121                                     391/131
CGG TAC CTA ATT TCT TAT GGA AAA CAT ACA CTT GAT ATG TTA GAA AGT AGC CAA GAT AaC
R   Y   L   I   S   Y   G   K   H   T   L   D   M   L   E   S   S   Q   D   N
421/141                                     451/151
ATG AGG ACT TCT TGG GTT TCA CAA ATG TTT AGT GAA ATT GAT GTA GAT AAC CTT GGA CAT
M   R   T   S   W   V   S   Q   M   F   S   E   I   D   V   D   N   L   G   H
481/161                                     511/171
ATA ACT CTG TGT AAT GCT GTG CAA TGT ATC AGA AAC CTC AAT CCT GGT TTA AAA ACG AGC
I   T   L   C   N   A   V   Q   C   I   R   N   L   N   P   G   L   K   T   S
541/181                                     571/191
AAA ATT GAG CTT AAG TTC AAA GAA TTG CAT AAA TCA AAG GAC AAA GCT GGT ACC GAG GTC
K   I   E   L   K   F   K   E   L   H   K   S   K   D   K   A   G   T   E   V
601/201                                     631/211
ACA AAG GAA GAA TTT ATT GAG GTT TTT CAT GAG CTT TGT ACT AGA CCT GAA ATT TAT TTC
T   K   E   E   F   I   E   V   F   H   E   L   C   T   R   P   E   I   Y   F
661/221                                     691/231
CTT TTA GTT CAG TTT TCA AGC AAT AAA GAA TTC CTT GAT ACC AAG GAC CTT ATG ATG TTT
L   L   V   Q   F   S   S   N   K   E   F   L   D   T   K   D   L   M   M   F
721/241                                     751/251
CTT GAG GCA GAA CAG GGT GTG GCA CAT ATA AAT GAG GAA ATA AGC CTT GAA ATT ATT CAC
L   E   A   E   Q   G   V   A   H   I   N   E   E   I   S   L   E   I   I   H
781/261                                     811/271
AAA TAT GAA CCA TCC AAA GAG GGT CAG GAA AAG GGC TGG CTC TCC ATA GAC GGG TTC ACT
K   Y   E   P   S   K   E   G   Q   E   K   G   W   L   S   I   D   G   F   T
841/281                                     871/291
AAT TAC CTT ATG TCA CCT GAC TGT TAT ATA TTC GAT CCA GAA CAT AAG AAG GTC TGT CAG
N   Y   L   M   S   P   D   C   Y   I   F   D   P   E   H   K   K   V   C   Q
901/301                                     931/311
GAT ATG AAG CAA CCT CTG TCT CAT TAC TTT ATA AAC TCA TCT CAT AAT ACA TAC TTA ATA
D   M   K   Q   P   L   S   H   Y   F   I   N   S   S   H   N   T   Y   L   I
961/321                                     991/331
GAG GAT CAG TTC CGA GGT CCC TCC GAC ATC ACA GGA TAT ATT CGA GCT CTT AAA ATG GGT
E   D   Q   F   R   G   P   S   D   I   T   G   Y   I   R   A   L   K   M   G
1021/341                                    1051/351
TGC CGG AGT GTT GAA TTA GAT GTA TGG GAT GGG CCG GAC AAT GAA CCT GTA ATT TAC ACA
C   R   S   V   E   L   D   V   W   D   G   P   D   N   E   P   V   I   Y   T
1081/361                                    1111/371
GGC CAC ACC ATG ACC TCT CAG ATA GTT TTC CGC AGT GTC ATT GAT ATT ATT AAC AAG TAT
G   H   T   M   T   S   Q   I   V   F   R   S   V   I   D   I   I   N   K   Y
1141/381                                    1171/391
GCA TTC TTT GCT TCA GAG TAT CCT CTT ATC TTG TGT TTA GAA AAC CAC TGT TCC ATT AAA
A   F   F   A   S   E   Y   P   L   I   L   C   L   E   N   H   C   S   I   K
1201/401                                    1231/411
CAA CAG AAG GTA ATG GTT CAG CAC ATG AAG AAA CTT TTA GGA GAC AAG CTC TAT ACA ACA
Q   Q   K   V   M   V   Q   H   M   K   K   L   L   G   D   K   L   Y   T   T
1261/421                                    1291/431
```

FIG. 1B

```
TCA CCC AAT GTT GAG GAA TCT TAT CTA CCA TCC CCA GAT GTC CTG AAA GGG AAA ATA CTA
S   P   N   V   E   E   S   Y   L   P   S   P   D   V   L   K   G   K   I   L
1321/441                                1351/451
ATT AAA GCA AAG AAG CTG TCC TCA AAT TGT TCT GGG GTA GAA GGA GAT GTT ACT GAC GAA
I   K   A   K   K   L   S   S   N   C   S   G   V   E   G   D   V   T   D   E
1381/461                                1411/471
GAT GAA GGA GCA GAA ATG TCT CAG AGG ATG GGA AAA GAG AAC ATG GAG CAA CCC AAT AAT
D   E   G   A   E   M   S   Q   R   M   G   K   E   N   M   E   Q   P   N   N
1441/481                                1471/491
GTG CCT GTG AAG CGA TTT CAG CTT TGT AAA GAA CTG TCT GAA CTG GTC AGC ATC TGC AAA
V   P   V   K   R   F   Q   L   C   K   E   L   S   E   L   V   S   I   C   K
1501/501                                1531/511
TCA GTT CAG TTC AAA GAA TTT CAG GTG TCG TTT CAG GTT CAG AAG TAC TGG GAA GTC TGT
S   V   Q   F   K   E   F   Q   V   S   F   Q   V   Q   K   Y   W   E   V   C
1561/521                                1591/531
TCC TTT AAT GAA GTG CTT GCC AGC AAG TAC GCC AAT GAA AAT CCA GGG GAC TTT GTA AAT
S   F   N   E   V   L   A   S   K   Y   A   N   E   N   P   G   D   F   V   N
1621/541                                1651/551
TAC AAC AAA CGT TTT CTT GCT AGG GTT TTT CCC AGT CCA ATG AGA ATT GAT TCC AGT AAC
Y   N   K   R   F   L   A   R   V   F   P   S   P   M   R   I   D   S   S   N
1681/561                                1711/571
ATG AAT CCT CAA GAT TTT TGG AAA TGT GGT TGC CAA ATT GTA GCC ATG AAC TTT CAG ACA
M   N   P   Q   D   F   W   K   C   G   C   Q   I   V   A   M   N   F   Q   T
1741/581                                1771/591
CCA GGA CTG ATG ATG GAC CTG AAT ATT GGC TGG TTT AGG CAG AAC GGA AAC TGT GGC TAT
P   G   L   M   M   D   L   N   I   G   W   F   R   Q   N   G   N   C   G   Y
1801/601                                1831/611
GTC CTC CGG CCA GCC ATC ATG AGG GAG GAG GTC TCC TTC TTC AGC GCC AAT ACA AAA GAC
V   L   R   P   A   I   M   R   E   E   V   S   F   F   S   A   N   T   K   D
1861/621                                1891/631
TCT GTC CCA GGG GTC TCA CCT CAA CTT CTT CAC ATT AAA ATC ATC AGT GGG CAG AAC TTT
S   V   P   G   V   S   P   Q   L   L   H   I   K   I   I   S   G   Q   N   F
1921/641                                1951/651
CCC AAG CCC AAA GGA TCA GGT GCC AAA GGT GAT     GTA GAT CCT TAT GTC TAT GTT GAA
P   K   P   K   G   S   G   A   K   G   D   V   V   D   P   Y   V   Y   V   E
1981/661                                2011/671
ATC CAT GGA ATC CCT GCT GAT TGT GCA GAA CAA AGG ACA AAA ACA GTG CAC CAG AAT GAA
I   H   G   I   P   A   D   C   A   E   Q   R   T   K   T   V   H   Q   N   G
2041/681                                2071/691
GAC GCT CCC ATT TTT GAT GAA AGC TTT GAA TTT CAA ATC AAC CTG CCT GAA CTG GCC ATG
D   A   P   I   F   D   E   S   F   E   F   Q   I   N   L   P   E   L   A   M
2101/701                                2131/711
GTG CGC TTT GTA GTG CTG GAT GAT GAC TAC ATT GGG GAT GAA TTC ATG GGC CAG TAC ACA
V   R   F   V   V   L   D   D   D   Y   I   G   D   E   F   M   G   Q   Y   T
2161/721                                2191/731
ATT CCC TTT GAA TGT TTA CAG ACG GGC TAC CGC CAT GTC CCC CTG CAG TCC TTA ACT GGA
I   P   F   E   C   L   Q   T   G   Y   R   H   V   P   L   Q   S   L   T   G
2221/741                                2251/751
GAG GTC CTT GCA CAT GCT TCT TTA TTT GTC CAC GTG GCT ATT ACT AAC CGA AGA GTA GGA
E   V   L   A   H   A   S   L   F   V   H   V   A   I   T   N   R   R   V   G
2281/761                                2311/771
GGA AAG CCT CAT AAA AGG GGC CTT TCT GTG AGA AAA GGG AAG AAA TCC AGG GAA TAT GCA
G   K   P   H   K   R   G   L   S   V   R   K   G   K   K   S   R   E   Y   A
2341/781                                2371/791
TCT TTG AGA ACA CTG TGG ATT AAA ACC GTG GAT GAG GTA TTC AAG AAT GCC CAG CCC CCT
S   L   R   T   L   W   I   K   T   V   D   E   V   F   K   N   A   Q   P   P
2401/801                                2431/811
ATA CGG GAT GCC ACA GAT CTG AGA GAA AAC ATG CAG AAT GCG GTG GTG TCA TTC AAG GAG
I   R   D   A   T   D   L   R   E   N   M   Q   N   A   V   V   S   F   K   E
2461/821                                2491/831
CTG TGT GGC CTC TCC TCT GTG GCC     CTC ATG CAG TGC ATG TTG GCG GTG TCT CCC CGC
L   C   G   L   S   S   V   A   N   L   M   Q   C   M   L   A   V   S   P   R
2521/841                                2551/851
TTT CTG GGG CCC GAT AAC ACA CCC CTA GTG GTC CTA AAT CTC AGC GAG CAG TAC CCC ACA
F   L   G   P   D   N   T   P   L   V   V   L   N   L   S   E   Q   Y   P   T
```

FIG. 1C

```
2581/861                          2611/871
ATG GAG CTG CAG GGA ATT GTG TCG GAG GTT CTG AAG AAG ATC GTA ACA ACT TAT GAC ATG
 M   E   L   Q   G   I   V   S   E   V   L   K   K   I   V   T   T   Y   D   M
2641/881                          2671/891
ATG ATT CAG TCC CTC AAG GCG TTG ATT GAA AAT GCA GAT GCT GTA TAT GAA AAG ATC GTA
 M   I   Q   S   L   K   A   L   I   E   N   A   D   A   V   Y   E   K   I   V
2701/901                          2731/911
CAT TGT CAG AAG GCA GCC ATG GAA TTC CAT GAA CAC TTG CAC AGC ATA GGC ACC AAG GAA
 H   C   Q   K   A   A   M   E   F   H   E   H   L   H   S   I   G   T   K   E
2761/921                          2791/931
GGT TTG AAG GAA AGA AAA CTA CAA AAA GCA GTG GAG AGC TTT ACC TGG AAT ATT ACC ATC
 G   L   K   E   R   K   L   Q   K   A   V   E   S   F   T   W   N   I   T   I
2821/941                          2851/951
TTA AAG GGA CAA GCA GAT CTT TTG AAA TAT GCT AAG AAT GAG ACA TTG GAG AAC CTG AAA
 L   K   G   Q   A   D   L   L   K   Y   A   K   N   E   T   L   E   N   L   K
2881/961                          2911/971
CAA ATC CAT TTT GCT GCT GTT TCA TGT GGA CTG AAT AAA CCA GGC ACC GAA AAT GCT GAT
 Q   I   H   F   A   A   V   S   C   G   L   N   K   P   G   T   E   N   A   D
2941/981                          2971/991
GTC CAG AAG CCA CGC CGG AGC TTG GAA GTC ATA CCC GAA AAA GCA AAC GAT GAA ACT GGA
 V   Q   K   P   R   R   S   L   E   V   I   P   E   K   A   N   D   E   T   G
3001/1001
GAA TGA
 E   *
```

FIG. 2 atgccaacagagaagaagatcagcagtgcaagtgattgtattaattcaatggttgagggt
tcagaactcaaaaaggttcgctccaactctagaatttatcataggtactttctactggat
gctgacatgcagagcctaaggtgggagccatctaagaaggattctgagaaagccaagatt
gacattaaatccatcaaggaagtgagaacgggaaaaacacagacatattccgcagcaat
ggcatttctgaccagatatctgaagattgtgcgttttccgtcatatatggagagaattat
gagtcactggatttggttgccactctcgcagatgttgcaaacatctgggttacaggactg
cggtacctaatttcttatggaaaacatacacttgatatgttagaaagtagccaagataac
atgaggacttcttgggtttcacaaatgtttagtgaaattgatgtagataaccttggacat
ataactctgtgtaatgctgtgcaatgtatcagaaacctcaatcctggtttaaaaacgagc
aaaattgagcttaagttcaaagaattgcataaatcaaaggacaaagctggtaccgaggtc
acaaaggaagaatttattgaggtttttcatgagctttgtactagacctgaaatttatttc
cttttagttcagttttcaagcaataaagaattccttgataccaaggaccttatgatgttt
cttgaggcagaacagggtgtggcacatataaatgaggaaataagccttgaaattattcac
aaatatgaaccatccaaagagggtcaggaaaagggctggctctccatagacgggttcact
aattaccttatgtcacctgactgttatatattcgatccagaacataagaaggtctgtcag
gatatgaagcaacctctgtctcattactttataaactcatctcataatacatacttaata
gaggatcagttccgaggtccctccgacatcacaggatatattcgagctcttaaaatgggt
tgccggagtgttgaattagatgtatgggatgggccggacaatgaacctgtaatttacaca
ggccacaccatgacctctcagatagttttccgcagtgtcattgatattattaacaagtat
gcattctttgcttcagagtatcctcttatcttgtgtttagaaaaccactgttccattaaa
caacagaaggtaatggttcagcacatgaagaaacttttaggagacaagctctatacaaca
tcacccaatgttgaggaatcttatctaccatccccagatgtcctgaaaggaaaatacta
attaaagcaaagaagctgtcctcaaattgttctggggtagaaggagatgttactgacgaa
gatgaaggagcagaaatgtctcagaggatgggaaaagagaacatggagcaacccaataat
gtgcctgtgaagcgatttcagctttgtaaagaactgtctgaactggtcagcatctgcaaa
tcagttcagttcaaagaatttcaggtgtcgtttcaggttcagaagtactgggaagtctgt
tcctttaatgaagtgcttgccagcaagtacgccaatgaaaatccaggggactttgtaat
tacaacaaacgtttttcttgctagggtttttcccagtccaatgagaattgattccagtaac
atgaatcctcaagattttggaaatgtggttgccaaattgtagccatgaactttcagaca
ccaggactgatgatggacctgaatattggctggtttaggcagaacggaaactgtggctat
gtcctccggccagccatcatgagggaggaggtctccttcttcagcgccaatacaaaagac
tctgtcccaggggtctcacctcaacttcttcacattaaaatcatcagtgggcagaacttt
cccaagcccaaaggatcaggtgccaaaggtgatgtggtagatccttatgtctatgttgaa
atccatggaatccctgctgattgtgcagaacaaaggacaaaaacagtgcaccagaatgga
gacgctcccattttgatgaaagctttgaatttcaaatcaacctgcctgaactggccatg
gtgcgctttgtagtgctggatgatgactacattggggatgaattcatggccagtacaca
attccctttgaatgtttacagacgggctaccgccatgtcccccctgcagtccttaactgga
gaggtccttgcacatgcttctttatttgtccacgtggctattactaaccgaagagtagga
ggaaagcctcataaaggggcctttctgtgagaaaagggaagaaatccagggaatatgca
tctttgagaacactgtggattaaaaccgtggatgaggtattcaagaatgcccagcccct
atacgggatgccacagatctgagagaaaacatgcagaatgcggtggtgtcattcaaggag
ctgtgtggcctctcctctgtggccaatctcatgcagtgcatgttggcggtgtctccccgc
tttctgggcccgataacacaccccctagtggtcctaaatctcagcgagcagtaccccaca
atggagctgcagggaattgtgtcggaggttctgaagaagatcgtaacaacttatgacatg
atgattcagtccctcaaggcgttgattgaaaatgcagatgctgtatatgaaaagatcgta
cattgtcagaaggcagccatggaattccatgaacacttgcacagcataggcaccaaggaa
ggtttgaaggaaagaaaactacaaaaagcagtggagagctttacctggaatattaccatc
ttaaagggacaagcagatcttttgaaatatgctaagaatgagacattggagaacctgaaa
caaatccattttgctgctgtttcatgtggactgaataaaccaggcaccgaaaatgctgat
gtccagaagccacgccggagcttggaagtcatacccgaaaaagcaaacgatgaaactgga
gaatga (SEQ ID NO: 01)

FIG. 3

TGTTATTAATAAAAATAAAGGGCCAGAATTGTCTCAAAGGATGGGAAAAGAGATTGGGAC
CACCCCACCCATGGGCTTGTAAAGCGATTTAAGCTTTGCAAAGACCTGTCTTAAACTGGC
AGCATCTGTAAGTCAGTCCAGTTCAAGAAGTTCCAGGTGTCGTTTCAGGTGCAAAAGTAC
TGGGAAGTGTGTTCATTCAATGAAGTGCTAGCCAGTAAATACGCCAATGAGAATCCTGGG
GACTTTGTAAATTACAATAAGCGTTTCCTCGCCAGAGTCTTTCCTAGTCCAATGAGAATT
GATTCTAGTAACATGAACCCTCAAGATTTTTGGAAATGTGGCTGTCAAATCGTAGCCATG
AACTTTCAGACTCCAGGGCTAATGATGGATCTGAACATTGGCTGGTTTAGGCAGAATGGA
AACTGTGGCTATGTTCTTCGACCAGCCATCATGAGGGAAGAAGTCTCCTTCTTCAGTGCC
AACACAAAGGACTCTGTCCCTGGAGTTTCGCCTCAGTTGCTTCACATCAAAATCATCAGT
GGCCAGAACTTTCCCAAGCCCAAAGGGTCAGGTGCCAAAGGGGATGTGGTGGACCCTT
(SEQ ID NO: 03)

TGSICKSVQFKKFQVSFQVQKYWEVCSFNEVLASKYANENPGDFVNYNKRFLARVFPSPM
RIDSSNMNPQDFWKCGCQIVAMNFQTPGLMMDLNIGWFRQNGNCGYVLRPAIMREEVSFF
SANTDKSVPGVSPQLLHIKIISGQNFPKPKGSGAKGDVVDP (SEQ ID NO: 04)

FIG. 4

GAGCAAACCCCACGGCCTGCCCCGCCGGAGCACCATCATCAACGATGGCACGAAGCAGAA
AAGAGAGCGGAAGAAGACCGTGTCATTCAGCAGCATGCCAACAGAGAAGAAGATCAGCAG
TGCAAGCGACTGCATCAACTCAATGGTGGAGGGCTCTGAACTCAAGAAGGTTCGTTCAAA
CTCCAGAATTTACCATCGGTACTTTCTGCTGGACGCCGACATGCAAAGCCTGAGGTGGGA
GCCATCCAAGAAGGATTCTGAGAAAGCCAAGATTGACATCAAGTCCATCAAGGAAGTTAG
AACGGGGAAAAACACAGATATATTCCCGCAGCAATGGGCATTTCTGAGCAAATATCTGAA
AGATTGTGCGTTTTCAGTCATATATGGAGAAAATATGAGTCACTCCGATTTGGTTGCCAA
TTCTGCAGATGTTGCAAACATCTGGGTGACAGGACTCCGGTACCTGATTTCTTATGGGAA
ACATACACTTGATATGTTAGAAAGTAGCCAAGACAACATGAGGACTTGTTGGGTTTCACA
GATGTTTAGTGAAATTGATGTAGATGACCTTGGACATATAACTCTGTGTAATGCTGTTCA
GTGTATCAGAAACCTCAATCCTGGCTTAAAAACAAGCAAAATTGAGCTTAAGTTCAAAGA
ACTGCATAAATCAAAGGACAAAACTGGTACTGAAATCACAAAGGAAGAATTTGTTGAGGT
TTTTCATGAACTTTGCACTAGACCTGAAATTTACTTCCTTTTAGTTCAGTTTTCAAGCAA
TAAAGAATTCCTTGATACCAAGGACCTTATGATGTTTCTTGAGGCAGAACAGGGTGTAGC
ACATATAAATGAGGAAATAAGCCTGGAAATTATTCACAAATATGAGCCATCCAAAGAAGG
CCAGGAAAAGGGCTGGCTCTCCATAGATGGGTTCACTAATTACCTGATGTCACCTGATTG
TTACATCTTTGATCCGGAACATAAGAAGGTCTGTCAGGATATGAAGCAACCTCTGTCTCA
TTACTTCATAAACTCATCTCATAATACATACTTAATAGAGGACCAGTTCCCGGGTCCCTC
TGACATTACAGGATATATCCGTGCTCTTAAAATGGGTTGCAGGAGTGTTGAGTTGGATGT
GTGGGATGGGCCAGATAATGAGCCCGTGATTTACACAGGCCACACCATGACCTCTCAGAT
AGTCTTCCGCAGTGTCATCGATATCATTAACAAGTATGCATTCTTTGCTTCTGAGTATCC
TCTCATCCTGTGTTTAGAAAATCATTGTTCTATTAAACAACAAAAGGTGATGGTTCAACA
CATGAAGAAAATTTTAGGAGACAAGCTGTATACCACATCACCCAACATGGAGGAATCTTA
TCTACCATCCCCCGATGTCCTGAAAGGGAAAATACTAATCAAAGCAAAGAAGCTGTCTTC
AAATTGCTCTGGTGTGGAAGGGGATGTTACTGATGAAGATGAAGGGGCAGAAATGTCTCA
GAGGATGGGGAAAGAGAATGTGGAACAACCCAACCATGTGCCTGTGAAGCGATTTCAGCT
TTGCAAAGACCTGTCTGAACTGGTCAGCATCTGTAAGTCAGTCCAGTTCAAGGAGTTCCA
GGTGTCGTTTCAGGTGCAGAAGTACTGGGAAGTGTGTTCATTCAATGAAGTGCTAGCCAG
TAAATACGCCAATGAGAATCCTGGGGACTTTGTAAATTACAATAAGCGTTTCCTCGCCAG
AGTCTTTCCTAGTCCAATGAGAATTGATTCTAGTAACATGAACCCTCAAGATTTTTGGAA
ATGTGGCTGTCAAATCGTAGCCATGAACTTTCAGACTCCAGGGCTAATGATGGATCTGAA
CATTGGCTGGTTTAGGCAGAATGGAAACTGGGCGCTAGTTCTTCGACCAGCCATCATGAG
GGAAGAAGTCTCCTTCTTCAGTGCCAACACAAAGGACTCTGTCCCTGGAGTTTCGCCTCA
GTTGCTTCACATCAAAATCATCAGTGGCCAGAACTTTCCCAAGCCCAAAGGGTCAGGTGC
CAAAGGGGATGTGGTGGACCCCTTATGTCTATGTGGAAATCCATGGCATTCCTGCTGACTG
CGCAGAACAGAGGACGAAAACTGTGAACCAGAATGGAGATGCTCCTATGTTTGATGAAAG
CTTTGAATTTCAAATCAACCTCCCCGAACTAGCCATGGTGCGCTTTGTAGTGCTGGATGA
TGACTACATTGGCGATGAATTTATTGGCCAGTACACGATTCCCTTTGAATGTTTACAAAC
GGGCTACCGCCATGTGCCTCTGCAGTCCTTGACTGGAGAGGTCCTTGCCCATGCTTCTCT
GTTCGTCCACGTGGCTATTACTAACAGAAGAGGAGGAGGGAAGCCTCATAAACGGGGCCT
TTCTGTGAGGAAAGGGAAGAAGTCCCGGGAATATGCATCTCTGAGAACACTGTGGATTAA
AACTGTAGATGAGGTGTTCAAGAATGCCCAGCCCCCCATCCGGGATGCCACAGACCTGAG
AGAGAACATGCAGAATGCAGTGGTTTCTTTCAAGGAATTATGTGGCCTCTCCTCAGTGGC
CAACCTTATGCAGTGCATGCTGGCCGTGTCTCCTCGATTCCTGGGGCCTGACAATACTCC
CCTGGTGGTCTTGAATCTTAGTGAGCCCTACCCCACCATGGAACTGCAGGCCATCGTGCC
TGAGGTTCTGAAGAAGATCGTCACAACTTATGACATGATGATTCAGTCCCTCAAGGCACG
ATTGAAAATGCAGATGCTGTGTATGAAAAGATTGTGCACTGTCAGAAGGCAGCCATGGAA
TTTCATGAACACTTGCACAGCATAGGCACCAAGGAGGGACTGAAGGAACGGAAACTACAG
AAGGCGGTGGAGAGCTTTACCTGGAATATTACGATTTTAAAGGGACCTCGTGCCGAATTC
CTGCAGCCCG GGGGATCC (SEQ ID NO: 05)

FIG. 5

MPTEKKISSASDCINSMVEGSELKKVRSNSRIYHRYFLLDADMQSLRWEPSKKDSEKAKI
DIKSIKEVRTGKNTDIFPQQWAFLSKYLKDCAFSVIYGENMSHSDLVANSADVANIWVTG
LRYLISYGKHTLDMLESSQDNMRTCWVSQMFSEIDVDDLGHITLCNAVQCIRNLNPGLKT
SKIELKFKELHKSKDKTGTEITKEEFVEVFHELCTRPEIYFLLVQFSSNKEFLDTKDLMM
FLEAEQGVAHINEEISLEIIHKYEPSKEGQEKGWLSIDGFTNYLMSPDCYIFDPEHKKVC
QDMKQPLSHYFINSSHNTYLIEDQFPGPSDITGYIRALKMGCRSVELDVWDGPDNEPVIY
TGHTMTSQIVFRSVIDIINKYAFFASEYPLILCLENHCSIKQQKVMVQHMKKILGDKLYT
TSPNMEESYLPSPDVLKGKILIKAKKLSSNCSGVEGDVTDEDEGAEMSQRMGKENVEQPN
HVPVKRFQLCKDLSELVSICKSVQFKEFQVSFQVQKYWEVCSFNEVLASKYANENPGDFV
NYNKRFLARVFPSPMRIDSSNMNPQDFWKCGCQIVAMNFQTPGLMMDLNIGWFRQNGNWA
LVLRPAIMREEVSFFSANTKDSVPGVSPQLLHIKIISGQNFPKPKGSGAKGDVVDPYVYV
EIHGIPADCAEQRTKTVNQNGDAPMFDESFEFQINLPELAMVRFVVLDDDYIGDEFIGQY
TIPFECLQTGYRHVPLQSLTGEVLAHASLFVHVAITNRRGGGKPHKRGLSVRKGKKSREY
ASLRTLWIKTVDEVFKNAQPPIRDATDLRENMQNAVVSFKELCGLSSVANLMQCMLAVSP
RFLGPDNTPLVVLNLSEPYPTMELQAIVPEVLKKIVTTYDMMIQSLKARLKMQMLCMKRL
CTVRRQPWNFMNTCTA (SEQ ID NO:09)

A) DNA sequence of KIAA1092

CCGCGCGCGGCGGCCCGAGGCGGCGGCGGGGACGCGGGGACGCGAGGACGCGGCTTTGTGCAGGCGGGTC
GCGGGGCGCCCATGGCGGAGTGCGGCCGGGGGGGCGCCGCCGGCGGGGCCCTGCCCACCTCCCCGGGCCC
GGCCCTCGGCGCCAAGGGCGCCCTGAAAGCCGGAGTGGGGAAGGCGGTGGCGGGGGAGGTCGCCTCGGC
CACGGGCGGGCGCGCTATGACAGCGGCGGGGTTTCCAACGGAGACTGCAGCCTCGGCGTGTCCGGGGACG
AAGCCCGGGCTAGCCCTACCAGGGGACCCCGCGGCGTTGCGCTCGCCCCGACCCCCAGCGCGGTCGTCTG
TACCCTCCCCCGGGAGAGCAAGCCGGGCGGCCTGCCCCGCCGGAGCAGCATCATCAAGGATGGTACAAAA
CAGAAGAGGGAACGGAAAAAGACAGTCTCATTCAGCAGCATGCCAACAGAGAAGAAGATCAGCAGTGCAA
GTGATTGTATTAATTCAATGGTTGAGGGTTCAGAACTCAAAAAGGTTCGCTCCAACTCTAGAATTTATCA
TAGGTACTTTTTACTGGATGCTGACATGCAGAGCCTAAGGTGGGAGCCATCTAAGAAGGATTCTGAGAAA
GCCAAGATTGACATTAAATCCATCAAGGAAGTGAGAACAGGAAAAAACACAGACATATTCCGCAGCAATG
GCATTTCTGACCAGATATCTGAAGATTGTGCGTTTTCCGTCATATATGGAGAGAATTATGAGTCACTGGA
TTTGGTTGCCAACTCCGCAGATGTTGCAAACATCTGGGTTACAGGACTGCGGTACCTAATTTCTTATGGA
AAACATACACTTGATATGTTAGAAAGTAGCCAAGATAACATGAGGACTTCTTGGGTTTCACAAATGTTTA
GTGAAATTGATGTAGATAACCTTGGACATATAACTCTGTGTAATGCTGTGCAATGTATCAGAAACCTCAA
TCCTGGTTTAAAAACGAGCAAAATTGAGCTTAAGTTCAAAGAATTGCATAAATCAAAGGACAAAGCTGGT
ACCGAGGTCACAAAGGAAGAATTTATTGAGGTTTTTCATGAGCTTTGTACTAGACCTGAAATTTATTTCC
TTTTAGTTCAGTTTTCAAGCAATAAAGAATTCCTTGATACCAAGGACCTTATGATGTTTCTTGAGGCAGA
ACAGGGTGTGGCACATATAAATGAGGAAATAAGCCTTGAAATTATTCACAAATATGAACCATCCAAAGAG
GGTCAGGAAAAGGGCTGGCTCTCCATAGACGGGTTCACTAATTACCTTATGTCACCTGACTGTTATATAT
TCGATCCAGAACATAAGAAGGTCTGTCAGGATATGAAGCAACCTCTGTCTCATTACTTTATAAACTCATC
TCATAATACATACTTAATAGAGGATCAGTTCCGAGGTCCCTCCGACATCACAGGATATATTCGAGCTCTT
AAAATGGGTTGCCGGAGTGTTGAATTAGATGTATGGGATGGGCCGGACAATGAACCTGTAATTTACACAG
GCCACACCATGACCTCTCAGATAGTTTTCCGCAGTGTCATTGATATTATTAACAAGTATGCATTCTTTGC
TTCAGAGTATCCTCTTATCTTGTGTTTAGAAAACCACTGTTCCATTAAACAACAGAAGGTAATGGTTCAG
CACATGAAGAAACTTTTAGGAGACAAGCTCTATACAACATCACCCAATGTTGAGGAATCTTATCTACCAT
CCCCAGATGTCCTGAAAGGGAAAATACTAATTAAAGCAAAGAAGCTGTCCTCAAATTGCTCTGGGGTAGA
AGGAGATGTTACTGACGAAGATGAAGGAGCAGAAATGTCTCAGAGGATGGGAAAAGAGAACATGGAGCAA
CCCAATAATGTGCCTGTGAAGCGATTTCAGCTTTGTAAAGAACTGTCTGAACTGGTCAGCATCTGCAAAT
CAGTTCAGTTCAAAGAATTTCAGGTGTCGTTTCAGGTTCAGAAGTACTGGGAAGTCTGTTCCTTTAATGA
AGTGCTTGCCAGCAAGTACGCCAATGAAAATCCAGGGGACTTTGTAAATTACAACAAACGTTTTCTTGCT
AGGGTTTTTCCCAGTCCAATGAGAATTGATTCCAGTAACATGAATCCTCAAGATTTTTGGAAATGTGGTT
GCCAAATTGTAGCCATGAACTTTCAGACACCAGGACTGATGATGGACCTGAATATTGGCTGGTTTAGGCA
GAACGGAAACTGTGGCTATGTCCTCCGGCCAGCCATCATGAGGGAGGAGGTCTCCTTCTTCAGCGCCAAT
ACAAAAGACTCTGTCCCAGGGGTCTCACCTCAACTTCTTCACATTAAAATCATCAGTGGGCAGAACTTTC
CCAAGCCCAAAGGATCAGGTGCCAAAGGTGATGTGGTAGATCCTTATGTCTATGTTGAAATCCATGGAAT
CCCTGCTGATTGTGCAGAACAAAGGACAAAAACAGTGCACCAGAATGGAGACGCTCCCATTTTTGATGAA
AGCTTTGAATTTCAAATCAACCTGCCTGAACTGGCCATGGTGCGCTTTGTAGTGCTGGATGATGACTACA
TTGGGGATGAATTCATCGGCCAGTACACAATTCCCTTTGAATGTTTACAGACGGGCTACCGCCATGTCCC
CCTGCAGTCCTTAACTGGAGAGGTCCTTGCACATGCTTCTTTATTTGTCCACGTGGCTATTACTAACCGA
AGAGGAGGAGGAAAGCCTCATAAAAGGGGCCTTTCTGTGAGAAAAGGGAAGAAATCCAGGGAATATGCAT
CTTTGAGAACACTGTGGATTAAAACCGTGGATGAGGTATTCAAGAATGCCCAGCCCCCTATACGGGATGC
CACAGATCTGAGAGAAAACATGCAGAATGCGGTGGTGTCATTCAAGGAGCTGTGTGGCCTCTCCTCTGTG
GCCAATCTCATGCAGTGCATGTTGGCGGTGTCTCCCCGCTTTCTGGGGCCCGATAACACACCCCTAGTGG
TCCTAAATCTCAGCGAGCAGTACCCCACAATGGAGCTGCAGGGAATTGTGCCGGAGGTTCTGAAGAAGAT
CGTAACAACTTATGACATGATGATTCAGTCCCTCAAGGCGTTGATTGAAAATGCAGATGCTGTATATGAA
AAGATCGTACATTGTCAGAAGGCAGCCATGGAATTCCATGAACACTTGCACAGCATAGGCACCAAGGAAG
GTTTGAAGGAAAGAAAACTACAAAAAGCAGTGGAGAGCTTTACCTGGAATATTACCATCTTAAAGGACA
AGCAGATCTTTTGAAATATGCTAAGAATGAGACATTGGAGAACCTGAAACAAATCCATTTTGCTGCTGTT
TCATGTGGACTGAATAAACCAGGCACCGAAAATGCTGATGTCCAGAAGCCACGCCGGAGCTTGGAAGTCA
TACCCGAAAAAGCAAACGATGAAACTGGAGAATGAGGAAACTTACAATAAACCATTATGGAGTTTATAAC
TCTAGGACCAATTGTAGTCAGATGGGACATTTGCTTTGCACTCACTAATGAGAATAATATTCGGGATTTT
AAAGCACAACTGGAATAGCTAATTACAGTCTATTAAAACTGTGAATGTATGTAGCAATCCTGCGTGTGAA
GGCAAATAAACTCTTTAACAGGCAATTATATTGCTGGCCAAAATATGCTATATTTGTATACAAAGACATT
CTAACTCAGTTCCAGTATGAAGAAAGATTATTCACTCTAGCTCCACTGAGAAACATTTTCCTAAGTGAAA
ACAATTTCTTAAGATGGAAATGGATTGGATTGTCAAATTATTATTTATTGGAGAAAAAAACCTGATCTAC
ACATTTTTACTTATATGGGGTTGCCAGAGTCTCTGGGTTCTAGATGATTTTGGTGGCATGCTTGCTGAGC
CATAATTACTAAAGAGAATGTAAGTGGACGGGTTCCCTGAATCCCCGGGGTCCTTGGAGAGCCATCGAGG
AGAATGTGCAATTGGACTGAAGCTCCCTGGCTGAAGATACATGCCGAGTCAGCACATGGGTAGAGATGAT
GTAAAAGCAGCCAATCTGGAAACAATACATTGTAAATAGTTTTTCATTGTATGAAGTAGTGTTCACATTA
AAAAGATGTTTTATGAT

B) Protein sequence of KIAA1092

PRAAARGGGGDAGTRGRGFVQAGRGAPMAECGRGGAAGGALPTSPGPALGAKGALKAGVGEGGGGGGRLG
HGRARYDSGGVSNGDCSLGVSGDEARASPTRGPRGVALAPTPSAVVCTLPRESKPGGLPRRSSIIKDGTK
QKRERKKTVSFSSMPTEKKISSASDCINSMVEGSELKKVRSNSRIYHRYFLLDADMQSLRWEPSKKDSEK
AKIDIKSIKEVRTGKNTDIFRSNGISDQISEDCAFSVIYGENYESLDLVANSADVANIWVTGLRYLISYG
KHTLDMLESSQDNMRTSWVSQMFSEIDVDNLGHITLCNAVQCIRNLNPGLKTSKIELKFKELHKSKDKAG
TEVTKEEFIEVFHELCTRPEIYFLLVQFSSNKEFLDTKDLMMFLEAEQGVAHINEEISLEIIHKYEPSKE
GQEKGWLSIDGFTNYLMSPDCYIFDPEHKKVCQDMKQPLSHYFINSSHNTYLIEDQFRGPSDITGYIRAL
KMGCRSVELDVWDGPDNEPVIYTGHTMTSQIVFRSVIDIINKYAFFASEYPLILCLENHCSIKQQKVMVQ
HMKKLLGDKLYTTSPNVEESYLPSPDVLKGKILIKAKKLSSNCSGVEGDVTDEDEGAEMSQRMGKENMEQ
PNNVPVKRFQLCKELSELVSICKSVQFKEFQVSFQVQKYWEVCSFNEVLASKYANENPGDFVNYNKRFLA
RVFPSPMRIDSSNMNPQDFWKCGCQIVAMNFQTPGLMMDLNIGWFRQNGNCGYVLRPAIMREEVSFFSAN
TKDSVPGVSPQLLHIKIISGQNFPKPKGSGAKGDVVDPYVYVEIHGIPADCAEQRTKTVHQNGDAPIFDE
SFEFQINLPELAMVRFVVLDDDYIGDEFIGQYTIPFECLQTGYRHVPLQSLTGEVLAHASLFVHVAITNR
RGGGKPHKRGLSVRKGKKSREYASLRTLWIKTVDEVFKNAQPPIRDATDLRENMQNAVVSFKELCGLSSV
ANLMQCMLAVSPRFLGPDNTPLVVLNLSEQYPTMELQGIVPEVLKKIVTTYDMMIQSLKALIENADAVYE
KIVHCQKAAMEFHEHLHSIGTKEGLKERKLQKAVESFTWNITILKGQADLLKYAKNETLENLKQIHFAAV
SCGLNKPGTENADVQKPRRSLEVIPEKANDETGE

DIAGNOSTIC MARKER FOR NEUROLOGICAL CONDITIONS

CROSS-REFERENCE TO RELATED APPLICATIONS

This application claims priority to U.S. provisional patent application No. 60/159,622 (filed Oct. 14, 1999) the disclosure of which is expressly incorporated herein by reference, in its entirety and for all purposes.

FIELD OF THE INVENTION

The invention relates to a human phospholipase C expressed in the brain (B-PLC), and to compositions and methods useful for diagnosing and treating physiologic pathologic conditions mediated by B-PLC. The invention finds application in the medical sciences.

BACKGROUND OF THE INVENTION

Intracellular signaling in the central nervous system (CNS) occurs predominantly by chemical signaling in which neurotransmitter molecules are released from one cell upon a challenge and are received and translated in the other into an appropriate pattern of response by specialized, cell membrane spanning polypeptides termed receptors. Some cellular responses are mediated by G-protein coupled receptors (GPCRs), members of a large family of transmembrane receptors. Upon their activation by neurotransmitters, GPCRs stimulate the GTPase activity of bound G-proteins and the latter are released and can activate several intracellular effector systems within the cell, including phospholipase C.

Phospholipase C (PLC) is an enzyme that breaks down phosphatidylinositol, a component of plasma membrane highly enriched in the CNS, to two important intracellular signaling molecules: diacylglycerol (DAG) and inositol-1, 4,5-phosphate (IP3). Both DAG and IP3 can trigger numerous signaling cascades in response to extracellular stimuli to maintain normal cellular homeostasis in the case of normal neuronal activity, or, when the stimulus is associated with a neuropathologic challenge, to manage the balance between cell death and cell survival, repair and regeneration. DAGs activate an important intracellular kinase, protein kinase C, in $Ca^{2+}$-dependent manner, while IP3 activates specific receptors on the endoplasmic reticulum to release $Ca^{2+}$ from intracellular stores, as well as IP3-dependent kinase (IP3-K). Via these pathways, the PLC-mediated signaling impacts such cellular phenomena as neurotransmitter release, receptor desensitization, transcriptional activation.

Proteins with homology to PLCs, but apparently lacking lipase activity, are also known. Like PLCs, these proteins bind inositol-1,4,5-phosphate, and are believed to play roles in regulation of activities mediated by $IP_3$. See, e.g., Kanematsu et al., 1996, *Biochem J* 313:319–25.

SUMMARY OF THE INVENTION

In one aspect, the invention provides an isolated, substantially pure, or recombinant B-PLC polypeptide, or immunogenic fragment thereof, for example, a polypeptide having an amino acid sequence exactly or substantially (e.g., at least about 80% or about 90%) identical to SEQ ID NO:2 or SEQ ID NO:4 or a fragment of the full-length sequence (e.g., a fragment having at least about 20 contiguous amino acid residues exactly identical to SEQ ID NO:2). In one embodiment, the invention provides a fusion protein having a sequence of a B-PLC polypeptide. In embodiment, the polypeptide has $IP_3$ binding activity. In embodiments, the polypeptide has PLC catalytic activity.

In another aspect, the invention provides an isolated polynucleotide that encodes, or is complementary to a sequence that encodes, a B-PLC polypeptide (e.g., having a sequence of SEQ ID NO:2 or a fragment thereof). In embodiments, the isolated polynucleotide has at least 15, at least 50, or at least 100 or more contiguous bases identical or exactly complementary to SEQ ID NO:1. In one embodiment, the invention provides an isolated polynucleotide that selectively hybridizes under stringent hybridization conditions to a polynucleotide sequence of SEQ ID NO:1. The polynucleotides of the invention may be operably linked to a promoter. The invention further provides a recombinant vector (such as an expression vector) containing a B-PLC polynucleotide, as well as cells (e.g., eukaryotic, mammalian or human cells) that contain the vector.

In another aspect, the invention provides an antibody (e.g., a monoclonal antibody), or fragment thereof, wherein the antibody or antibody fragment specifically binds to a B-PLC polypeptide.

In one aspect, the invention provides a method of detecting an B-PLC gene product in a sample by (a) contacting the sample with a probe that specifically binds the gene product, wherein the probe and the gene product form a complex, and detecting the formation of the complex; or (b) specifically amplifying the gene product in the biological sample, wherein said gene product is a polynucleotide, and detecting the amplification product; where the formation of the complex or presence of the amplification product is correlated with the presence of the B-PLC gene product in the biological sample. In this assay, the sample may be from human. The gene product may be, in various embodiments, a protein or RNA, and the probe may be an antibody or polynucleotide.

In a different aspect, the invention provides a method of treating an B-PLC mediated condition in a mammal by modulating (e.g., increasing or reducing) the activity or expression of B-PLC in a cell or tissue in the mammal.

The invention further provides methods for the diagnosis of a neurological condition in an animal, such as a human patient, by obtaining a biological sample from the animal and detecting an increased level of B-PLC in the sample compared to the level in a healthy animal, wherein said increased level is diagnostic of a neurological condition in the animal. In an embodiment the biological sample is blood. In an embodiment, the method of claim 17 wherein the increased level of B-PLC is detected using an immunoassay. The neurological condition that can be diagnosed may be hypoxic-ischemic brain insult (e.g., stroke), a neuroinflammatory disease, or other conditions.

Any method of detection can be used. In an embodiment, the increased level of B-PLC is detected using a detectably labeled polynucleotide probe comprising the sequence of SEQ ID NO:1 or 6 or a fragment thereof. In a different embodiment the the increased level of B-PLC is detected using an antibody that specifically binds the polypeptide of SEQ ID NO: 2 or 7.

In another aspect, the invention provides a method of treating a condition characterized by increased B-PLC expression in a mammal comprising modulating the activity or expression of B-PLC in a cell or tissue in the mammal. Examples of conditions susceptible to treatment include hypoxic-ischemic brain insult (e.g., stroke).

In another aspect, the invention provides a method of identifying an agent that modulates of B-PLC activity comprising contacting a cell or composition comprising a B-PLC protein encoded by a B-PLC polynucleotide and detecting a difference in protein activity in the presence of the agent compared to the absence of the agent. In embodiment the activity is IP3-binding activity.

A method of identifying an agent that modulates of B-PLC expression in a cell, comprising contacting a cell that expresses the B-PLC protein of SEQ ID NO:2 or a naturally occurring allele thereof, and detecting a change in B-PLC expression in the presence of the agent compared to the absence of the agent.

The invention also provides a method for identifying an agent for treatment or prevention of a neurological condition (e.g., hypoxic-ischemic brain insult), by determining whether a compound or treatment is a modulator of activity or expression of a B-PLC. In an embodiment, the activity is $IP_3$-binding activity.

BRIEF DESCRIPTION OF THE FIGURES

FIGS. 1*a*, 1*b*, 1*c* show the nucleotide sequence for a human B-PLC (SEQ. ID NO:1) coding region and the predicted amino acid sequence of the human B-PLC polypeptide (SEQ. ID NO:2).

FIG. 2 shows the nucleotide sequence for a full-length human B-PLC cDNA (SEQ ID NO:8).

FIG. 3 shows the nucleotide (SEQ. ID NO:3) of a portion of a partial rat B-PLC cDNA, as determined from an expressed sequence tag (EST) from a library of ESTs enriched for sequences overexpressed in ischemic brain. The conceptual amino acid sequence (SEQ. ID NO:4) is also shown.

FIG. 4 shows the nucleotide sequence (SEQ. ID NO:5) of a nearly full-length clone of rat B-PLC corresponding to the EST clone of SEQ. ID. NO.:3 (with the boundaries of the EST sequence indicated).

FIG. 5 shows the conceptual translation of the polynucleotide shown in FIG. 4 (SEQ ID NO:9).

FIG. 8*a* shows the nucleotide sequence and

FIG. 8*b* shows the amino acid sequence of Clone KIAA1092 (Genbank ID AB029015).

DETAILED DESCRIPTION

I. Definitions

Figure 6:
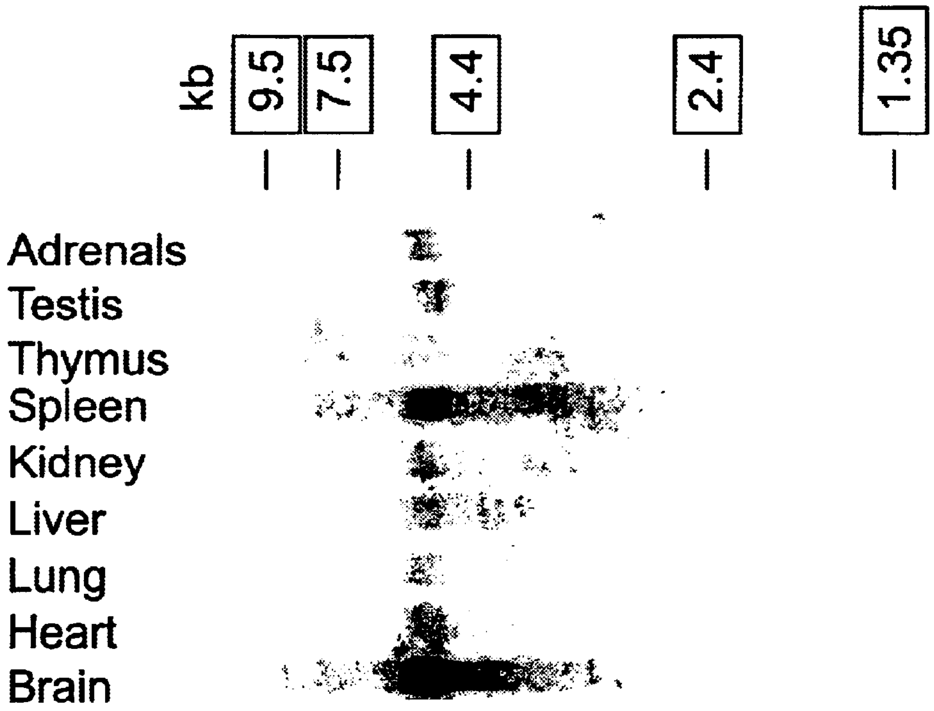
FIG. 6 shows the hybridization pattern of hB-PLC specific cDNA to the panel of mRNAs from various tissues.

The following definitions are provided to assist the reader in the practice of the invention.

The terms "allele" or "allelic sequence," as used herein, refer to a naturally-occurring alternative form of a gene encoding the B-PLC polypeptide (i.e., a polynucleotide encoding an B-PLC polypeptide). Alleles result from mutations (i.e., changes in the nucleic acid sequence), and generally produce altered and/or differently regulated mRNAs or polypeptides whose structure and/or function may or may not be altered. Common mutational changes that give rise to alleles are generally ascribed to natural deletions, additions, or substitutions of nucleotides that may or may not affect the encoded amino acids. Each of these types of changes may occur alone, in combination with the others, or one or more times within a given gene, chromosome or other cellular polynucleotide. Any given gene may have no, one or many allelic forms. As used herein, the term "allele" refers to either or both a gene or an mRNA transcribed from the gene.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "antisense sequences" refers to polynucleotides having sequence complementary to a RNA sequence. These terms specifically encompass nucleic acid sequences that bind to mRNA or portions thereof to block transcription of mRNA by ribosomes. Antisense methods are generally well known in the art (see, e.g., PCT publication WO 94/12633, and Nielsen et al., 1991, *Science* 254:1497; OLIGONUCLEOTIDES AND ANALOGUES, A PRACTICAL APPROACH, edited by F. Eckstein, IRL Press at Oxford University Press (1991); ANTISENSE RESEARCH AND APPLICATIONS (1993, CRC Press)).

The term "conservative substitution," when describing a polypeptide, refers to a change in the amino acid composition of the polypeptide that does not substantially alter the activity of the polypeptide, i.e., substitution of amino acids with other amino acids having similar properties such that the substitutions of even critical amino acids does not substantially alter activity. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see also, Creighton, 1984, *Proteins*, W. H. Freeman and Company).

In addition to the above-defined conservative substitutions, other type of conservative modification of amino acid residues can result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, e.g., often less than 5%, in an encoded sequence can also be Further, a conservatively modified variant can be made from a recombinant polypeptide by substituting a codon for an amino acid employed by the native or wild-type gene with a different codon for the same amino acid.

The terms "control elements" or "regulatory sequences" include enhancers, promoters, transcription terminators, origins of replication, chromosomal integration sequences, 5' and 3' untranslated regions, with which polypeptides or other biomolecules interact to carry out transcription and translation. For eukaryotic cells, the control sequences will include a promoter and preferably an enhancer, e.g., derived from immunoglobulin genes, SV40, cytomegalovirus, and a polyadenylation sequence, and may include splice donor and acceptor sequences. Depending on the vector system and host utilized, any number of suitable transcription and translation elements, including constitutive and inducible promoters, may be used.

As used herein, a "derivatized" polynucleotide, oligonucleotide, or nucleic acid refers to oligo- and polynucleotides that comprise a derivatized substituent. In some embodiments, the substituent is substantially non-interfering with respect to hybridization to complementary polynucleotides. Derivatized oligo- or polynucleotides that have been modified with appended chemical substituents (e.g., by modification of an already synthesized oligo- or polynucleotide, or by incorporation of a modified base or backbone analog during synthesis) may be introduced into a metabolically active eukaryotic cell to hybridize with an B-PLC DNA, RNA, or protein where they produce an alteration or chemical modification to a local DNA, RNA, or protein. Alternatively, the derivatized oligo or polynucleotides may interact with and alter B-PLC polypeptides, or proteins that interact with B-PLC DNA or B-PLC gene products, or alter or modulate expression or function of B-PLC DNA, RNA or protein. Illustrative attached chemical substituents include: europium (III) texaphyrin, cross-linking agents, psoralen, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/EDTA chelates are chemical substituents often used where local cleavage of a nucleic acid sequence is desired (Hertzberg et al., 1982, *J. Am. Chem. Soc.* 104: 313; Hertzberg and Dervan, 1984, *Biochemistry* 23: 3934; Taylor et al., 1984, *Tetrahedron* 40: 457; Dervan, 1986, *Science* 232: 464). Illustrative attachment chemistries include: direct linkage, e.g., via an appended reactive amino group (Corey and Schultz, 1988, *Science* 238: 1401, which is incorporated herein by reference) and other direct linkage chemistries, although streptavidin/biotin and digoxigenin/anti-digoxigenin antibody linkage methods can also be used. Methods for linking chemical substituents are provided in U.S. Pat. Nos. 5,135,720, 5,093,245, and 5,055,556, which are incorporated herein by reference. Other linkage chemistries may be used at the discretion of the practitioner.

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical, chemical means and the like.

The term "epitope" has its ordinary meaning of a site on an antigen recognized by an antibody. Epitopes are typically segments of amino acids which are a small portion of the whole polypeptide. Epitopes may be conformational (i.e., discontinuous). That is, they may be formed from amino acids encoded by noncontiguous parts of a primary sequence that have been juxtaposed by protein folding.

The term "fusion protein," refers to a composite polypeptide, i.e., a single contiguous amino acid sequence, made up of two (or more) distinct, heterologous polypeptides which are not normally fused together in a single amino acid sequence. Thus, a fusion protein may include a single amino acid sequence that contains two entirely distinct amino acid sequences or two similar or identical polypeptide sequences, provided that these sequences are not normally found together in the same configuration in a single amino acid sequence found in nature. Fusion proteins may generally be prepared using either recombinant nucleic acid methods, i.e., as a result of transcription and translation of a recombinant gene fusion product, which fusion comprises a segment encoding a polypeptide of the invention and a segment encoding a heterologous polypeptide, or by chemical synthesis methods well known in the art.

The term "gene product" refers to an RNA molecule transcribed from a gene, or a polypeptide encoded by the gene or translated from the RNA.

The term "high affinity" for an IgG antibody, as used herein, refers to an association constant (Ka) of at least about $10^6 M^{-1}$, preferably at least about $10^8 M^{-1}$, more preferably at least about $10^9 M^{-1}$ or greater, e.g., up to $10^{12} M^{-1}$ or greater. However, "high affinity" binding can vary for other antibody isotypes.

The terms "immunogen" and "immunogenic" have their ordinary meaning in the art, i.e., an immunogen is a molecule, such as a polypeptide or other antigen, that can elicit an adaptive immune response upon injection into a person or an animal.

The terms "nucleic acid" and "polynucleotide" are used interchangeably and refer to deoxyribonucleotides or ribonucleotides and polymers thereof in either single-or double-stranded form. Unless specifically limited, the disclosure of a polynucleotide sequence is also intended to refer to the complementary sequence. As used herein, the term "polynucleotide" includes oligonucleotides (i.e., short polynucleotides, e.g., typically at least about 7 bases).

The terms "oligonucleotides" or "oligomers" refer to a nucleic acid sequence of approximately 7 nucleotides or greater, and as many as approximately 100 nucleotides, which can be used as a primer or probe. Oligonucleotides are often between about 10 and about 50 nucleotides in length, more often between about 12 and about 50 nucleotides, very often between about 15 and about 25 nucleotides.

The term "operably linked" refers to a functional relationship between two or more polynucleotide (e.g., DNA) segments: for example, a promoter or enhancer is operably linked to a coding sequence if it stimulates the transcription of the sequence in an appropriate host cell or other expression system. Generally, sequences that are operably linked are contiguous, and in the case of a signal sequence both contiguous and in reading phase. However, enhancers need not be located in close proximity to the coding sequences whose transcription they enhance. The terms "peptidomimetic" and "mimetic" refer to a synthetic chemical compound which has substantially the same structural and functional characteristics of the B-PLC polypeptides of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, J. Adv. Drug Res. 15:29 (1986); Veber and Freidinger TINS p.392 (1985); and Evans et al. J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a phospholipase C polypeptide, but have one or more peptide linkages optionally replaced by a linkage selected from the group consisting of, e.g., —CH2NH—, —CH2S—, —CH2—CH2—, —CH═CH— (cis and trans), —COCH2—, —CH(OH)CH2—, and —CH2SO—.

The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the enzymatic activities of B-PLC.

The term "polypeptide" is used interchangeably herein with the term "protein," and refers to a polymer composed of amino acid residues linked by amide linkages, including synthetic, naturally-occurring and non-naturally occurring analogs thereof (amino acids and linkages). Peptides are examples of polypeptides.

As used herein, a "probe" refers to a molecule that specifically binds another molecule. One example of a probe is a "nucleic acid probe," which can be a DNA, RNA, or other polynucleotide. Where a specific sequence for a nucleic acid probe is given, it is understood that the complementary strand is also identified and included. The complementary strand will work equally well in situations where the target is a double-stranded nucleic acid that specifically binds (e.g., anneals or hybridizes) to a substantially complementary nucleic acid. Another example of a probe is an "antibody probe" that specifically binds to a corresponding antigen or epitope.

The term "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process is use of recombinant nucleic acid techniques, e.g., involving human intervention in the nucleotide sequence, typically selection or production. Alternatively, it can be a polynucleotide made by generating a sequence comprising fusion of two fragments which are not naturally contiguous to each other, but is meant to exclude products of nature. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

The phrase "selectively hybridizing to" refers to a polynucleotide probe that hybridizes, duplexes or binds to a particular target DNA or RNA sequence when the target sequences are present in a preparation of total cellular DNA or RNA.

The phrase "specifically immunoreactive," or "specifically binds" when referring to the interaction between an antibody and a protein or polypeptide, refers to an antibody that specifically recognizes and binds with relatively high affinity to the protein of interest, e.g., B-PLC, such that this binding is determinative of the presence of the protein in a heterogeneous population of proteins and other biologics. Thus, under designated immunoassay conditions, the specified antibodies bind to a particular polypeptide and do not bind in a significant amount to other polypeptides present in the sample. A variety of immunoassay formats may be used to select antibodies specifically immunoreactive with a particular polypeptide. For example, solid-phase ELISA immunoassays are routinely used to select monoclonal antibodies specifically immunoreactive with a polypeptide. See, Harlow, 1988, ANTIBODIES, A LABORATORY MANUAL, Cold Spring Harbor Publications, New York (hereinafter, "Harlow"), for a description of immunoassay formats and conditions that can be used to determine specific immunoreactivity.

As used herein, the "substantially sequence identity," refers to two or more sequences or subsequences that have at least 60%, preferably 80%, most preferably 90%, 95%, 98%, or 99% nucleotide or amino acid residue identity, when compared and aligned for maximum correspondence, as measured using one of the following sequence comparison algorithms or by visual inspection. Two sequence (amino acid or nucleotide) can be compared over their full-length (e.g., the length of the shorter of the two, if they are of substantially different lengths) or over a subsequence such as at least about 50, about 100, about 200, about 500 or about 1000 contiguous nucleotides or at least about 10, about 20, about 30, about 50 or about 100 contiguous amino acid residues.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols In Molecular Biology, Greene Publishing and Wiley-Interscience, New York (supplemented through 1999). Each of these references and algorithms is incorporated by reference herein in its entirety. When using any of the aforementioned algorithms, the default parameters for "Window" length. gap penalty, etc., are used.

One example of algorithm that is suitable for determining percent sequence identity and sequence similarity is the BLAST algorithm, which is described in Altschul et al., J. Mol. Biol., 215:403410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, Proc. Natl. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Alignments may also be carried out using CLUSTAL (Higgins et al., CLUSTAL V: multiple alignment of DNA and protein sequences. *Methods Mol Biol* 1994; 25:307–18) using the default parameters.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions.

Another indication that two nucleic acid sequences are substantially identical is that the two molecules hybridize to each other under stringent conditions. Substantial identity exists when the segments will hybridize under stringent hybridization conditions to a strand, or its complement, typically using a sequence of at least about 50 contiguous nucleotides derived from the probe nucleotide sequences. “Stringent hybridization conditions” refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel (1987) Methods In Enzymology, Vol. 152: Guide To Molecular Cloning Techniques, San Diego: Academic Press, Inc. and Sambrook et al., et al., 1989, MOLECULAR CLONING: A LABORATORY MANUAL, (2nd ed.) Vols. 1–3, Cold Spring Harbor Laboratory. As indicated by standard references, a simple estimate of the Tm value may be calculated by the equation: Tm=81.5+0.41(% G+C), when a nucleic acid is in aqueous solution at 1 M NaCl (see e.g., Anderson and Young, “Quantitative Filter Hybridization” in Nucleic Acid Hybridization (1985)). Other references include more sophisticated computations which take structural as well as sequence characteristics into account for the calculation of Tm. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed.

The terms “substantially pure” or “isolated,” when referring to proteins and polypeptides, e.g., B-PLC, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition. When referring to polynucleotides, the terms “substantially pure” or “isolated” generally refer to the polynucleotide separated from contaminants with which it is generally associated, e.g., lipids, proteins and other polynucleotides. The substantially pure or isolated polynucleotides of the present invention will be greater than about 50% pure. Typically, these polynucleotides will be more than about 60% pure, more typically, from about 75% to about 90% pure and preferably from about 95% to about 98% pure.

The following sections provide guidance for making and using the compositions of the invention, and carrying out the methods of the invention.

II. Introduction

The mammalian brain has a limited capacity to survive long periods of hypoxia and ischemia (lack of oxygen and blood supply). Following exposure to hypoxia-ischemia, neurons affected by this treatment die by rapid or slow mechanisms of cell death (necrosis or apoptosis). Hypoxic-ischemic brain insults, such as stroke, neonatal asphyxia, heart failure (resulting in prolonged lack of blood supply to the brain), or drowning, can cause severe permanent brain damage. On the other hand, brief, sublethal periods of hypoxia-ischemia can lead to a transient phase in the brain when neurons become protected from subsequent injury and death. This treatment, generally referred to as ischemic tolerance, or ischemic preconditioning, can provide the basis for and lead to an understanding of intrinsic protective mechanisms and pathways through endogenous proteins or factors that provide for this effect. The present invention relates to a phospholipase C expressed in brain (e.g., hippocampus and cerebral cortex, the regions of brain containing neurons most vulnerable in ischemic stroke) in response to ischemic preconditioning.

The specificity and selectivity of the activation of a particular PLC in a given cell is determined by the presence in the cell of G protein coupled receptors (GPCR), the subset of G-proteins capable of conveying the extracellular stimulus from the GPCR to the PLC, and expression of the particular PLC. The present invention provides B-PLC polynucleotides and polypeptides useful for diagnosis and treatment of pathological conditions in humans and non-human animals. "B-PLC" refers to a phospholipase C-like protein expressed in brain as further described herein.

In one embodiment, the invention provides a novel B-PLC polynucleotides and polypeptides (including human and rodent homologs) discovered by the inventors as described in Examples 1 and 2 (e.g., SEQ ID NOS:1–5, 8, and 9 and related molecules and variants thereof). Further, as shown in Example 4, infra, it has been discovered by the present inventors that increased expression of the B-PLC of the invention occurs under conditions of ischemia. It will be recognized from this discovery that detection of such increased expression is useful in diagnosis and prognosis of ischemia (or other neuronal damage) in a patient or model animal. Reagents useful in the methods of the invention (e.g., detection, diagnostic, and therapeutic methods) include the B-PLC molecules specifically exemplified in Examples 1 and 2, infra, and Clone KIAA1092 (a longer variant of B-PLC).

III. B-PLC Polypeptides

The present invention provides isolated, substantially pure, or recombinant B-PLC polypeptides and immunogenic fragments of mammalian B-PLC polypeptides. In one embodiment, the B-PLC polypeptide or fragment has an amino acid sequence identical to, or substantially identical to, the sequence set forth in SEQ ID NO:2 or a subsequence thereof. In another embodiment, the B-PLC polypeptide or fragment has an amino acid sequence identical to, or substantially identical to, the sequence set forth in FIG. 5 (SEQ ID NO:9) or a subsequence thereof (e.g., SEQ ID NO:4). In one embodiment, a polypeptide having a sequence of SEQ ID NO:7 is used in the methods of the invention (e.g., diagnostic, therapeutic, and screening methods), in preparation pharmaceutical compositions, and the like.

The various protein domains present in the B-PLC polypeptide (e.g., SEQ ID NO:2) serve different functional purposes. Two domains termed the X and Y regions are present in PLCs and they associate tightly to form the active catalytic center of the enzyme. The pleckstrin homology (PH) domain in the N-terminus of B-PLC is known to attach the members of PLC family to membranous phosphoinositols (PIP2) prior to their actual cleavage by PLC activity. The EF-hand $Ca^{2+}$-binding domain as well as two essential histidine residues in the catalytic active site domain X mediate the $Ca^{2+}$-dependence of the enzymatic reaction. The C2 domain in the C-terminal half of B-PLC has been suggested to be involved in the Ca2+-dependent binding of PLCs to lipid vesicles as well as in interactions with signaling G-proteins. B-PLC and other known PLCs (except PLCγ) lack SH2 or SH3 domains, which participate in protein-protein interactions with members of the PLCγ family.

PLCs are members of a superfamily of PLCs that has been divided into different classes: PLC-α, PLC-β, PLC-γ, PLC-δ and PLC-ε. Although B-PLC displays sequence similarity to PLC-δ throughout its protein coding sequence except in the elongated C-terminus which bears more resemblance to PLC-β, it is likeliest that B-PLC may form a family together PLC-ε, with which it shares about 66% identity at the amino acid level.

The following functional domains were detected in the predicted protein sequence using PROSITE database of protein motifs (Henikoff et al. 1991, Nucleic Acids Res. 19: 6565–72). (The numbering refers to the amino acid sequence):

- a.a. 15–127 pleckstrin homology domain
- a.a. 146–209 EF-hand Ca2+-binding domain
- a.a. 300–444 PIP2-dependent phospholipase C catalytic region X
- a.a. 419–608 PIP2-dependent phospholipase C catalytic region Y
- a.a. 615–711 C2-domain In an embodiment, the B-PLC polypeptides of the invention have $IP_3$-binding activity. $IP_3$-binding of a protein can be detected using any of a variety routine assays known in the art (including assays described infra). In an embodiment, a B-PLC polypeptide of the invention has phospholipase catalytic activity. Catalytic activity can be detected using any of a variety routine assays known in the art (including assays listed infra). Two residues involved in catalytic activity (His356, Tyr552) are absent in B-PLC polypeptide. The invention therefor contemplates variants of the exemplified sequences in which residues Thr(360) and Phe(550) of SEQ ID NO:2 (or corresponding residues in other B-PLCs) are mutated (using standard mean, see, e.g., Ausubel, supra) to His and Tyr, respectively.

B-PLC is expressed at high levels in brain in many cell types including the majority of forebrain neurons as well as glial cells. Its activity there can thus be activated by many types of neurotransmitters and modulators (glutamate, acetylcholine, noradrenaline, dopamine, serotonin, bioactive lipids, various neuropeptides and chemotactic cytokines) which are released to the synaptic cleft during normal and abnormal brain activity to elicit responses at their respective GPCRs. Most probably the signals from GPCRs to B-PLC are conveyed by $G_q$ or $G_{11}$. The two main cellular signaling pathways whose engagement depends on PLC, most probably also in cells harboring B-PLC, are the DAG/PKC and IP3/intracellular $Ca^{2+}$ release pathways. Both of these pathways have been linked excitotoxic and apoptotic cellular phenomena in neurons, hence the modulation of B-PLC activity (e.g., $IP_3$-binding activity) will alleviate the negative impact of above-mentioned events to the fate of neurons exposed to challenge. Furthermore, chemotaxis of microglia/monocytes to the locus of damage induced upon injury or challenge by chemokines is known to be accompanied by elevated intracellular $Ca^{2+}$ levels as a result of increased PLC activity, probably that of B-PLC, in those cells. Thus, modulators of B-PLC activity are useful to circumvent undesired consequences of what the action of microglia/monocytes might do to neurons or to any others cells in the damaged area or its proximity if left uncontrolled.

PLC domains, activities, and interactions are discussed in Rhee et al. *J Biol Chem*. 1997 (272) 15045–8, and Singer et al. *Annu Rev Biochem*. 1997;66:475–509, incorporated herein by reference.

A. B-PLC Polypeptides and Variants

The invention provides substantially pure, isolated, or recombinant B-PLC polypeptides. In some embodiments, the B-PLC polypeptide has an amino acid sequence identical or substantially identical to the amino acid sequence shown in SEQ ID NO:2. In other embodiments, the B-PLC polypeptides are variants and mutants characterized by conservative substitutions of amino acid residues of SEQ ID NO:2.

The polypeptide of the invention may be full-length (e.g., containing about 1000 amino acids for the species shown in FIGS. 1 and 4) or may encode a fragment of the full-length protein. In various embodiments, the fragments may have at least about 16, at least about 25, at least about 35, or at least about 50 residues identical to a region of SEQ ID NO: 2, 5, or 9. The full length B-PLC polypeptides of the invention typically have a calculated molecular weight of from about 110 to about 120 kDa. Also provided by the invention are B-PLC polypeptides that are modified, relative to the amino acid sequence of SEQ ID NO:2, in some manner, e.g., truncated, mutated, derivatized, or fused to other sequences (e.g., to form a fusion protein). Some B-PLC polypeptides comprise insertions, deletions or substitutions of amino acid residues relative to SEQ ID NO:2, or SEQ ID NO:9. For example, some conservative amino acid substitutions can be made, i.e., substitution of selected amino acids with different amino acids having similar structural characteristics, e.g., net charge, hydrophobicity, and the like.

The modified B-PLC polypeptides of the invention can have some or all of the biological activities of naturally-occurring, full-length B-PLC. These activities include binding of the polypeptides to PIP2-enriched cell membranes, binding of IP3, sensing $Ca^{2+}$ levels inside the cell, and catalytic activity (eg. enzymatic breakdown of PIP2 to IP3 and DAG to regulate intracellular signal transduction by elevating $Ca^{2+}$ levels and increasing PKC-mediated phosphorylation, respectively). The above-mentioned signaling pathways can modulate neurotransmitter release and sensitivity of plasma membrane receptors to extracellular stimuli, i.e. intercellular communication, as well as determining cell fate. These activities may be assayed using standard routine assays. For example, a cell-based system which co-expresses B-PLC together with activating GPCRs (receptors to glutamate, acetylcholine, noradrenaline, dopamine, serotonin, various neuropeptides and chemotactic cytokines) and a reporter gene operationally linked to a promoter activated by PLC (such as ICAM reporter (Weyer U, et al. Receptors Channels 1 (1993), 193–200) can be used. Alternatively, instead of using a reporter gene, the kinetics of the B-PLC-dependent breakdown of PIP2 to IP3 and DAG can be determined by chromatographic analysis, e.g. by HPLC, or, when using radioactively labeled PIP2, by measuring radioactivity of particular cellular fractions. Alternatively, a reconstituted system consisting of PIP2-enriched lipid micelles and purified or recombinantly expressed B-PLC, GPCR and $G\alpha_q$ or $G\alpha_{11}$ subunits of G-proteins in combination with its various Pγ—subunits can be utilized to assess the enzymatic activity of B-PLC (Lee, S. B. and Rhee, S. G., Curr. Opin. Cell Biol. 7 (1995) 183–89).

In some embodiments the B-PLC polypeptides or fragments of the invention have a phospholipase activity. Assays for phospholipase activity are well known in the art, see, e.g., Krug and Kent, 1981, METHODS ENZYMOL 72:347–51, and include phospholipase C-phosphatase coupled assays, classical radiochemical techniques (e.g., solution based radiolabeled mixed phospholipid micelle methods), bioluminescence assays, fluorescence quenching assays, and spectrophotometric techniques (e.g., Farooqui et al., 1984, *J Lipid Res* 25:1555–62), use of FlashPlates (Mullinax et al., "Monitoring Inositol-Specific Phospholipase C Activity Using a Phospholipid FlashPlate" NEN Life Science Products, Boston, Mass., and others known in the art. Each of the aforementioned articles is incorporated by reference herein in its entirety and for all purposes. In one embodiment, phospholipase activity is measured using the phospholipase C-phosphatase coupled assay described by Krug and Kent, supra. Suitable assays are also described in Krug and Kent, Arch. Biochem. Biophys. 231:400–410 (1984), which are incorporated herein by reference). Also, PLC activity can be determined by the hydrolysis of p-nitrophenylphosphorylcholine, Berka et al, 1982, J. Bacteriol. 152:239–245 and, which is incorporated herein by reference). All of the aforementioned references are incorporated herein by reference in their entirety and for all purposes.

Another activity of PLC proteins is $IP_3$-binding activity. Thus, it is apparent that the B-PLC of the invention bind $IP_3$. $IP_3$ binding can be detected using any standard assay. In one embodiment a fusion protein comprising an eptiope tag (e.g., glutathione S-transferase, GST) and the B-PLC coding region are expressed and purified (e.g., using a glutathione column). In a particular embodiment, the purified fusion proteins are incubated with radiolabled $IP_3$, (e.g., $^3H$—Ins (1,3,5) $P_3$) in 50 μl of buffer for 30 min at room temperature. Then 10 μl of bovine γ-globulin (30 mg/ml) and one ml of 20% polyethyleneglycol 6000 are added and the tubes incubated for 30 min on ice. After centrifugaton at 100,000×g for 10 min, the precipitates are dissolved in 100 μl of 0.1 N NaOH, and then the radioactivity was measured. In an embodiment, binding is detected when radioactivity is greater than background (e.g., in the absense of B-PLC protein, e.g. at least 2-fold greater).

In some embodiments, the B-PLC polypeptide of the invention is used as an immunogen (e.g., to produce anti-B-PLC antibodies). Typically, the immunogenic B-PLC fragments of the invention comprise at least about 6 contiguous residues of the B-PLC sequence, e.g., SEQ ID NO:2, more often at least about 8, about 15, or about 20, or about 25 contiguous residues. In some embodiments, the B-PLC polypeptide encoded by SEQ ID NO:9 is used as an immunogen to produce antibodies useful in the diagnostic assays of the invention.

The substantially pure, isolated or recombinant B-PLC polypeptides of the resent invention can also be characterized by their ability to bind antibodies that are pecifically immunoreactive with a polypeptide having the sequence shown in SEQ ID NO:2. Specific immunoreactivity is usually characterized by a specific binding affinity of an antibody for its ligand (e.g., B-PLC) of at least $10^7$, $10^8$, $10^9$, or $10^{10}$ $M^{-1}$.

For many applications, it will also be desirable to provide B-PLC polypeptides of the invention as labeled entities, i.e., covalently attached or linked to a detectable label or group, or cross-linkable group, to facilitate identification, detection and quantification of the polypeptide in a given circumstance. These detectable groups can comprise a detectable polypeptide group, e.g., an assayable enzyme or antibody epitope. Alternatively, the detectable group can be selected from a variety of other detectable groups or labels, such as radiolabels (e.g., $^{125}I$, $^{32}P$, $^{35}S$) or a chemiluminescent or fluorescent group. Similarly, the detectable group can be a substrate, cofactor, inhibitor or affinity ligand.

In addition, a B-PLC polypeptide can be modified by substituting one or more amino acid residues with a D-amino acid of the same type (e.g., D-lysine in place of L-lysine) to generate more stable peptides. Similarly, modification of the amino or carboxyl terminals can also be used to confer stabilizing properties upon the polypeptides of the invention, e.g., amidation of the carboxyl-tenninus or acylation of the amino-terminus or pegylated derivatives.

B-PLC variants, including variants with conservative or nonconservative amino acid substitutions are useful as agonists and antagonists of B-PLC activity. For example, modification of key amino acid residues in the active site regions X and Y (e.g. histidine residues in positions 315 and 362 SEQ ID NO:2) of B-PLC as well as those in domains that determine the Ca2+-dependence (EF-hand, C2-domain) are expected to render it enzymatically inactive. Such "dominant negative" B-PLC variants, i.e., B-PLC polypeptides which are capable of binding the substrate, but not turning it over, may be used as a competitive inhibitor of B-PLC, and can be used to down-regulate excessive B-PLC activity in conditions where it could be undesirable (Beekman A, et al. Cancer Res. 1998 (58) 910–3).

Elsewhere, mutations of amino acid residues involved in receiving the G-protein input from GPCRs, for example in the C2 domain, are used to alter responsiveness of B-PLC to a particular signaling pathway. Mutations of some nonessential amino acid residues in or near the active site regions X and Y can lead to B-PLC variants with elevated activity or to constitutively active B-PLC species. The latter can be used to compensate B-PLC deficiency in conditions where such inadequacies might occur. Variant B-PLCs can be constructed for in vivo expression in appropriate gene delivery vehicles such as adenoviral or similar vectors.

In various embodiment, the polypeptide of the invention are at least about 10, about 50, about 100, about 250, about 500 or about 1000 amino acid residues in length.

B. Production and Isolation of B-PLC Polypeptides

The B-PLC polypeptides of the present invention can be prepared using recombinant or synthetic methods, or can be isolated from natural cellular sources.

Suitable recombinant techniques for expressing B-PLC polypeptides from the B-PLC polynucleotides are disclosed infra. See also, Sambrook et al., 1989, MOLECULAR CLONING: A LABORATORY MANUAL, (2nd ed.) Vols. 1–3, Cold Spring Harbor Laboratory, and in Ausubel, supra. Synthetic methods for synthesizing polypeptides such as B-PLC polypeptides, variants, or fragments are described in Merrifield, 1963, *Amer. Chem. Soc.* 85:2149–2456, Atherton et al., 1989, SOLID PHASE PEPTIDE SYNTHESIS: A PRACTICAL APPROACH, IRL Press, and Merrifield, 1986, *Science* 232:341–347.

Isolation and purification of the B-PLC polypeptides of the present invention can be carried out by methods that are generally well known in the art. These methods include, but are not limited to, ion exchange, hydrophobic interaction, HPLC or affinity chromatography, to achieve the desired purity. In one embodiment, B-PLC polypeptides are purified using immunoaffinity chromatography. For example, antibodies raised against a B-PLC polypeptide or immunogenic fragment thereof (e.g., having a sequence or subsequence of SEQ ID NO:2) are coupled to a suitable solid support and contacted with a mixture of polypeptides containing the B-PLC polypeptide (e.g., a homogenate of brain tissue) under conditions conducive to the association of this polypeptide with the antibody. Once the B-PLC polypeptide is bound to the immobilized antibody, the solid support is washed to remove unbound material and/or nonspecifically bound polypeptides. The desired polypeptide can then be eluted from the solid support in substantially pure form by, e.g., a change in pH or salt concentration of the buffer.

C. Peptide Analogs and Peptide Mimetics of B-PLC

Although primarily described in terms of "proteins" or "polypeptides," one of skill in the art will understand that structural analogs and derivatives of the above-described polypeptides, e.g., peptidomimetics, and the like can be used as substitutes for B-PLC, e.g., as B-PLC activity agonists, or, alternatively, as B-PLC activity antagonists. Peptidomimetics, or peptide mimetics, are peptide analogs commonly used in the pharmaceutical industry as non-peptide drugs with properties (e.g., a biological activity) analogous to those of the template peptide. (Fauchere, 1986, *Adv. Drug Res.* 15:29; Evans et al., 1987, *J. Med. Chem.* 30:1229). They are usually developed with the aid of computerized molecular modeling. Peptide mimetics that are structurally similar to therapeutically useful peptides can be used to produce an equivalent therapeutic effect. Peptide mimetics can have significant advantages over polypeptide embodiments, including, for example, more economical production and greater chemical stability.

IV. B-PLC Polynucleotides

In one aspect, the invention provides a polynucleotide having a sequence or subsequence of a mammalian (e.g., rat or human) B-PLC gene or RNA. The polynucleotides of the invention (e.g., RNA, DNA, PNA or chimeras), and may be single-stranded, double stranded, or a mixed hybrid. In one embodiment, the polynucleotide has a sequence of SEQ. ID NO:8 (FIG. 2) or NO:5 (FIG. 4) or subsequences thereof. The invention also provides polynucleotides with substantial sequence identity to the B-PLC polynucleotides disclosed herein. Thus, the invention provides naturally occurring alleles of mammalian (e.g., rat and human) B-PLC genes and variant polynucleotide sequences having one or more nucleotide deletions, insertions or substitutions relative to a B-PLC nucleic acid sequence disclosed herein.

As described infra, in some embodiments the polynucleotide of the invention encodes a polypeptide with substantial sequence similarity to SEQ. ID NO:2 (FIG. 1) or encodes a fragment of such a polypeptide (e.g., a fusion protein). Also contemplated are polynucleotides that, due to the degeneracy of the genetic code, are not substantially similar to SEQ ID NO:1, but encode the polypeptide of SEQ. ID NO:2 or a fragment thereof. In other embodiments, the invention provides B-PLC polynucleotides that do not necessarily encode B-PLC polypeptide but which are useful as e.g., probes, primers, antisense, triplex, or ribozyme reagents, and the like.

The invention also includes expression vectors, cell lines, and transgenic organisms comprising the B-PLC polynucleotides. In some embodiments, the vectors, cells, and organisms of the invention are capable of expressing the encoded B-PLC polypeptides.

Using the guidance of this disclosure, the B-PLC polynucleotides of the invention can be produced by recombinant means. See, e.g., Sambrook et al., (1989) Molecular Cloning: A Laboratory Manual, 2nd Ed., Vols. 1–3, Cold Spring Harbor Laboratory; Berger and Kimmel, (1987) Methods In Enzymology, Vol. 152: Guide To Molecular Cloning Techniques, San Diego: Academic Press, Inc.; Ausubel et al., Current Protocols In Molecular Biology, Greene Publishing and Wiley-Interscience, New York (1999). Alternatively, B-PLC polynucleotides or fragments can be chemically synthesized using routine methods well known in the art (see, e.g., Narang et al., 1979, *Meth. Enzymol.* 68:90; Brown et al., 1979, *Meth. Enzymol.* 68:109; Beaucage et al., 1981, *Tetra. Lett.*, 22:1859). In some embodiments, the B-PLC polynucleotides of the invention contain non-naturally occurring bases, e.g., deoxyinosine (see, Batzer et al., 1991, Nucleic Acid Res. 19:5081; Ohtsuka et al., 1985, J. Biol. Chem. 260:2605–2608; Rossolini et al., 1994, Mol. Cell. Probes 8:91–98) or modified backbone residues or linkages.

In various embodiments, polynucleotide of the invention is at least about 50, about 100, about 200, about 500, about 1000, about 2000 or about 3000 bases or basepairs in length.

A. Polynucleotides Encoding B-PLC

In one aspect, the invention provides polynucleotides encoding B-PLC polypeptides such as an B-PLC polypeptide comprising the sequence of SEQ ID NO:2, a fragment thereof, a variant thereof (e.g., a conservative or allelic variant), or a B-PLC fusion polypeptide. In one embodiment, the polynucleotide of the invention comprises the sequence of SEQ ID NO:1 or a fragment thereof. In another embodiment, the polynucleotide encodes a naturally occurring B-PLC polypeptide or fragment, but has a sequence that differs from SEQ. ID NO:1 (e.g., as a result of the degeneracy of the genetic code).

The polynucleotides of invention are useful for expression of B-PLC polynucleotides (e.g., sense or antisense RNAs) and polypeptides. Methods for recombinant expression of polynucleotides and proteins are well known in the art. Typically, the B-PLC polynucleotides of the invention are used in expression vectors for the preparation of B-PLC polypeptides and polynucleotides. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells.

In one embodiment, DNA encoding an B-PLC polypeptide of the present invention is inserted into DNA constructs capable of introduction into and expression in an in vitro host cell, such as a bacterial (e.g., *E. coli, Bacillus subtilus*), yeast (e.g., Saccharomyces), insect (e.g., *Spodoptera frugiperda*), or mammalian cell culture systems. Examples of mammalian cell culture systems useful for expression and production of the polypeptides of the present invention include human embryonic kidney line (293; Graham et al., 1977, *J. Gen. Virol.* 36:59); CHO (ATCC CCL 61 and CRL 9618); human cervical carcinoma cells (HeLa, ATCC CCL 2); and others known in the art. The use of mammalian tissue cell culture to express polypeptides is discussed generally in Winnacker, FROM GENES TO CLONES (VCH Publishers, N.Y., N.Y., 1987) and Ausubel, supra.

In some embodiments, promoters from mammalian genes or from mammalian viruses are used, e.g., for expression in mammalian cell lines. Suitable promoters can be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, and promoter-enhancer combinations known in the art.

B-PLC polypeptides or fragments can also be expressed in transgenic animals (mouse, sheep, cow, etc.) and plants (tobacco, arabidopsis, etc.) using appropriate expression vectors which integrate into the host cell chromosome.

B. Polynucleotide or Oligonucleotide Probes and Primers

In one embodiment, the invention provides oligonucleotide or polynucleotide probes and/or primers for detecting or amplifying B-PLC polynucleotides. In various embodiments, the polynucleotides (e.g., probes and primers) comprise at least 10 contiguous bases identical or exactly complementary to SEQ ID NO:1 or NO:3, usually at least 12 bases, typically at least 15 bases, generally at least 18 bases and often at least 25, at least 50, or at least 100 bases When the B-PLC polynucleotides of the invention are used as probes or primers they are generally less that about 3000 bases in length; typically they contain between about 12 and about 100 contiguous nucleotides identical or exactly complementary to SEQ. ID NO:1 or NO:5, more often between about 12 and about 50 contiguous nucleotides, even more often between about 15 and about 25 contiguous nucleotides. In some embodiments of the invention, probes and primers having a sequence of SEQ ID NO:7, or a fragment thereof, are used in the methods (e.g., diagnostic, therapeutic methods, and screening methods) of the invention, in preparation pharmaceutical compositions, and the like.

In some embodiments, the probes and primers are modified, e.g., by adding restriction sites to the probes or primers. In other embodiments, primers or probes of the invention comprise additional sequences, such as linkers. In still some other embodiments, primers or probes of the invention are modified with detectable labels. For example, the primers and probes are chemically modified, e.g., derivatized, incorporating modified nucleotide bases, or containing a ligand capable of being bound by an anti-ligand (e.g., biotin).

The B-PLC primers of the invention can be used for a number of purposes, e.g., for amplifying an B-PLC polynucleotide in a biological sample for detection, or for cloning B-PLC genes from a variety of species. Using the guidance of the present disclosure, primers can be designed for amplification of the human B-PLC gene or regions encoding particular protein domains of the B-PLC gene. Exemplary primer pairs for amplifying domains are described in Table 1.

| Domain to be amplified | Primer Pair |
|---|---|
| PH Domain | 5' TATTAATTCAATGGTTGAG 3' (SEQ ID NO:10) |
| | 5' AAGTGTATGTTTTCCATAAG 3' (SEQ ID NO:11) |
| EF-hand | 5' AGATAACATGAGGACTTG 3' (SEQ ID NO12) |
| | 5' ACAAAGCTCATGAAAAACC 3' (SEQ ID NO:13) |
| PLC X-region | 5' AGAACATAAGAAGGTCTGTC 3' (SEQ ID NO:14) |
| | 5' GTATTTTCCCTTTCAGCAG 3' (SEQ ID NO:15) |
| PLC Y-region | 5' GAGAACATGGAGCAACCC 3' (SEQ ID NO:16) |
| | 5' CCTCATGATGGCTGGCCGG 3' (SEQ ID NO:17) |
| C2-domain | 5' GAGGGAGGAGGTCTCCTTC 3' (SEQ ID NO:18) |
| | 5' AATTGTGTACTGGCCCATG 3' (SEQ ID NO:19) |

C. B-PLC Inhibitor Polynucleotides

The invention provides inhibitory polynucleotides such as antisense, triplex, and ribozyme reagents that target or hybridize to B-PLC polynucleotides. These polynucleotides may be used to treat disease states which are associated with elevated activity of B-PLC leading to rapid changes in intracellular $Ca^{2+}$ levels and/or in PKC signaling. Acute neurodegenerative conditions such as ischemic stroke, head trauma or injury are prime candidates, as well as neuroinflammatory diseases with consequences to neurons.

1. Antisense Polynucleotides

In one aspect, the present invention provides antisense oligonucleotides and polynucleotides that can be used to inhibit expression of the B-PLC gene. Some therapeutic methods of the invention, described in additional detail infra, involve the administration of an oligonucleotide that functions to inhibit or stimulate B-PLC activity under in vivo physiological conditions, and is relatively stable under those conditions for a period of time sufficient for a therapeutic effect. Polynucleotides can be modified to impart such stability and to facilitate targeting delivery of the oligonucleotide to the desired tissue, organ, or cell.

The antisense polynucleotides of the invention comprise an antisense sequence of at least about 10 bases, typically at least 20, at least about 50, or at least about 100, and up to at least about 1000 to at least about 3000 contiguous nucleotides that specifically hybridize to a sequence from mRNA encoding B-PLC or mRNA transcribed from the B-PLC gene. More often, the antisense polynucleotide of the invention is from about 12 to about 50 nucleotides in length or from about 15 to about 25 nucleotides in length. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors.

Generally, to assure specific hybridization, the antisense sequence is substantially complementary to the target B-PLC mRNA sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to B-PLC RNA or its gene is retained as a functional property of the polynucleotide.

In one embodiment, the antisense sequence is complementary to relatively accessible sequences of the B-PLC mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Examples of oligonucleotides that may be tested in cells for antisense suppression of B-PLC function are those capable of hybridizing to (i.e., substantially complementary to) SEQUENCE ID NO:1, for example, 5'-ATT GGG TTG CTC CAT-3' (SEQ ID NO:20) and 5'-TAG AAA GTA CCT ATG A-3' (SEQ ID NO:21). Another useful method for identifying effective antisense compositions uses combinatorial arrays of oligonucleotides (see, e.g., Milner et al., 1997, *Nature Biotechnology* 15:537).

The invention also provides an antisense polynucleotide that has sequences in addition to the antisense sequence (i.e., in addition to anti-B-PLC-sense sequence). In this case, the antisense sequence is contained within a polynucleotide of longer sequence. In another embodiment, the sequence of the polynucleotide consists essentially of, or is, the antisense sequence.

The antisense nucleic acids (DNA, RNA, modified, analogues, and the like) can be made using any suitable method for producing a nucleic acid, such as the chemical synthesis and recombinant methods disclosed herein. In one embodiment, for example, antisense RNA molecules of the invention may be prepared by de novo chemical synthesis or by cloning. For example, an antisense RNA that hybridizes to B-PLC mRNA can be made by inserting (ligating) an B-PLC DNA sequence (e.g., SEQ. ID No; 1, or fragment thereof) in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

The antisense oligonucleotides of the invention can be used to inhibit B-PLC activity in cell-free extracts, cells, and animals, including mammals and humans. An example of a suitable antisense oligonucleotide is phosphorothioate antisense oligonucleotide having the sequence

5'-AGGATTCTCATTGGCGTATTTACTGGCTAGCA CTTCATTG-3'(SEQ ID NO:22)

For general methods relating to antisense polynucleotides, see ANTISENSE RNA AND DNA, (1988), D.A. Melton, Ed., Cold Spring Harbor Laboratory, Cold Spring Harbor, N.Y.). See also, Dagle et al., 1991, *Nucleic Acids Research*, 19:1805. For a review of antisense therapy, see, e.g., Uhlmann et al., *Chem. Reviews*, 90:543–584 (1990).

2. Triplex Oligo- and Polynucleotides

The present invention provides oligo- and polynucleotides (e.g., DNA, RNA, PNA or the like) that bind to double-stranded or duplex B-PLC nucleic acids (e.g., in a folded region of the B-PLC RNA or in the B-PLC gene), forming a triple helix-containing, or Atriplex≅nucleic acid. Triple helix formation results in inhibition of B-PLC expression by, for example, preventing transcription of the B-PLC gene, thus reducing or eliminating B-PLC activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides of the invention are constructed using the base-pairing rules of triple helix formation (see, e.g., Cheng et al., 1988, *J. Biol. Chem.* 263: 15110; Ferrin and Camerini-Otero, 1991, *Science* 354:1494; Ramdas et al., 1989, *J. Biol. Chem.* 264:17395; Strobel et al., 1991, *Science* 254:1639; and Rigas et al., 1986, *Proc. Natl. Acad Sci. U.S.A.* 83: 9591; each of which is incorporated herein by reference) and the B-PLC mRNA and/or gene sequence. Typically, the triplex-forming oligonucleotides of the invention comprise a specific sequence of from about 10 to at least about 25 nucleotides or longer complementary to a specific sequence in the B-PLC RNA or gene (i.e., large enough to form a stable triple helix, but small enough, depending on the mode of delivery, to administer in vivo, if desired). In this context, Acomplementary≅means able to form a stable triple helix. In one embodiment, oligonucleotides are designed to bind specifically to the regulatory regions of the B-PLC gene (e.g., the B-PLC 5'-flanking sequence, promoters, and enhancers) or to the transcription initiation site, (e.g., between −10 and +10 from the transcription initiation site). For a review of recent therapeutic advances using triplex DNA, see Gee et al., in Huber and Carr, 1994, MOLECULAR AND IMMUNOLOGIC APPROACHES, Futura Publishing Co, Mt Kisco N.Y. and Rininsland et al., 1997, *Proc. Natl. Acad. Sci. USA* 94:5854, which are both incorporated herein by reference.

3. Ribozymes

The present invention also provides ribozymes useful for inhibition of B-PLC activity. The ribozymes of the invention bind and specifically cleave and inactivate B-PLC mRNA. Useful ribozymes can comprise 5'- and 3'-terminal sequences complementary to the B-PLC mRNA and can be engineered by one of skill on the basis of the B-PLC mRNA sequence disclosed herein (see PCT publication WO 93/23572, supra). Ribozymes of the invention include those having characteristics of group I intron ribozymes (Cech, 1995*, Biotechnology* 13:323) and others of hammerhead ribozymes (Edgington, 1992*, Biotechnology* 10:256).

Ribozymes of the invention include those having cleavage sites such as GUA, GUU and GUC. Other optimum cleavage sites for ribozyme-mediated inhibition of B-PLC activity in accordance with the present invention include those described in PCT publications WO 94/02595 and WO 93/23569, both incorporated herein by reference. Short RNA oligonucleotides between 15 and 20 ribonucleotides in length corresponding to the region of the target B-PLC gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assays, or by testing for in vitro ribozyme activity in accordance with standard procedures known in the art.

As described by Hu et al., PCT publication WO 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

In one embodiment, the ribozymes of the invention are generated in vitro and introduced into a cell or patient. In another embodiment, gene therapy methods are used for expression of ribozymes in a target cell ex vivo or in vivo.

4. Administration of Oligonucleotides

In an embodiment, the therapeutic methods of the invention involve the administration of an oligonucleotide that functions to inhibit or stimulate B-PLC activity under in vivo physiological conditions, and is relatively stable under those conditions for a period of time sufficient for a therapeutic effect. As noted above, modified nucleic acids may be useful in imparting such stability, as well as for targeting delivery of the oligonucleotide to the desired tissue, organ, or cell.

Oligo- and poly-nucleotides can be delivered directly as a drug in a suitable pharmaceutical formulation, or indirectly by means of introducing a nucleic acid into a cell, including liposomes, immunoliposomes, ballistics, direct uptake into cells, and the like as described herein. For treatment of disease, the oligonucleotides of the invention will be administered to a patient in a therapeutically effective amount. A therapeutically effective amount is an amount sufficient to ameliorate the symptoms of the disease or modulate B-PLC activity in the target cell, e.g., as can be measured using a using a cell based assay, e.g., as described in §III(A), supra. Methods useful for delivery of oligonucleotides for therapeutic purposes are described in U.S. Pat. No. 5,272,065, incorporated herein by reference. Other details of administration of pharmaceutically active compounds are provided below. In another embodiment, oligo- and polynucleotides can be delivered using gene therapy and recombinant DNA expression plasmids of the invention. It will be recognized to those of skill that, to administer antibodies or therapeutic oligonucleotides to the brain, it is sometime necessary administer via intracerebroventricular injections or other direct administration mode.

D. Allelic Variants and Homologs of B-PLC Polynucleotides

The invention also provides human allelic variants of the B-PLC polynucleotides of SEQ ID NO:1, and non-human homologs of B-PLC. The polynucleotide probes of the invention are used for isolating and expressing B-PLC from humans and non-human animals, using well known methods, e.g., Sambrook, supra, and Ausubel, supra. For example, a polynucleotide probe comprising all or some of the B-PLC cDNA sequence is labeled and used to screen a genomic or cDNA library by hybridization at moderate stringency (e.g., hybridization in 5×SSC/50% formamide at 42C for 16 h, and wash in 0.1×SSC/0.1% SDS at 50C for 30 min.). The cDNA library can be oligo-dT or random primed. The cDNA or genomic clones that hybridize with the probe are isolated and analyzed by restriction mapping, Southern hybridization, and DNA sequencing using methods that are well known in the art. Depending on the starting library used, a polynucleotide comprising human B-PLC gene, allelic cDNAs, or B-PLC homologs from non-human species can be isolated. B-PLC alleles and homologs can be assayed for various activities characteristic of B-PLC.

Another method for generating B-PLC variants having a desired activity is by directed evolution or "gene shuffling," as described, for example in Patten et al., 1997*, Curr. Opin. Biotech*. 8:724–733; PCT publications WO95/22625; WO97/20078; WO97/35957; WO97/35966; WO98/13487; WO98/13485; PCT 98/00852; PCT 97/24239, and U.S. Pat. No. 5,605,793.

E. Gene Therapy

Gene therapy refers to the introduction of an otherwise exogenous polynucleotide which produces a medically useful phenotypic effect upon the (typically) mammalian cell(s) into which it is transferred. In one aspect, the present invention provides gene therapy methods and compositions for treatment of B-PLC-associated conditions. In illustrative embodiments, gene therapy involves introducing into a cell a vector that expresses an B-PLC gene product (such as an B-PLC protein substantially similar to the B-PLC polypeptide having a sequence of SEQUENCE ID NO: 2 or 7, e.g., to increase B-PLC activity, or an inhibitory B-PLC polypeptide to reduce activity), expresses a nucleic acid having an B-PLC gene or mRNA sequence (such as an antisense RNA, e.g., to reduce B-PLC activity), expresses a polypeptide or polynucleotide that otherwise affects expression of B-PLC gene products (e.g., a ribozyme directed to B-PLC mRNA to reduce B-PLC activity), or replaces or disrupts an endogenous B-PLC sequence (e.g., gene replacement and Agene knockout, ≅respectively). Numerous other embodiments will be evident to one of skill upon review of the disclosure herein.

Vectors useful in B-PLC gene therapy can be viral or nonviral, and include those described supra in relation to the B-PLC expression systems of the invention. It will be understood by those of skill in the art that gene therapy vectors may comprise promoters and other regulatory or processing sequences, such as are described in this disclosure. Usually the vector will comprise a promoter and, optionally, an enhancer (separate from any contained within the promoter sequences) that serve to drive transcription of an oligoribonucleotide, as well as other regulatory elements that provide for episomal maintenance or chromosomal integration and for high-level transcription, if desired. A plasmid useful for gene therapy can comprise other functional elements, such as selectable markers, identification regions, and other sequences. The additional sequences can have roles in conferring stability both outside and within a cell, targeting delivery of B-PLC nucleotide sequences (sense or antisense) to a specified organ, tissue, or cell population, mediating entry into a cell, mediating entry into the nucleus of a cell and/or mediating integration within nuclear DNA. For example, aptamer-like DNA structures, or other protein binding moieties sites can be used to mediate binding of a vector to cell surface receptors or to serum proteins that bind to a receptor thereby increasing the efficiency of DNA transfer into the cell. Other DNA sites and structures can directly or indirectly bind to receptors in the nuclear membrane or to other proteins that go into the nucleus, thereby facilitating nuclear uptake of a vector. Other DNA sequences can directly or indirectly affect the efficiency of integration.

Suitable gene therapy vectors may, or may not, have an origin of replication. For example, it is useful to include an origin of replication in a vector for propagation of the vector prior to administration to a patient. However, the origin of replication can often be removed before administration if the vector is designed to integrate into host chromosomal DNA or bind to host mRNA or DNA.

As noted, the present invention also provides methods and reagents for gene replacement therapy (i.e., replacement by homologous recombination of an endogenous B-PLC gene with a recombinant gene). Vectors specifically designed for integration by homologous recombination may be used. Important factors for optimizing homologous recombination include the degree of sequence identity and length of homology to chromosomal sequences. The specific sequence mediating homologous recombination is also important, because integration occurs much more easily in transcriptionally active DNA. Methods and materials for constructing homologous targeting constructs are described by e.g., Mansour et al., 1988*, Nature* 336: 348; Bradley et al., 1992*, Bio/Technology* 10: 534. See also, U.S. Pat. Nos. 5,627,059; 5,487,992; 5,631,153; and 5,464,764. In one embodiment, gene replacement therapy involves altering or replacing all or a portion of the regulatory sequences controlling expression of the B-PLC gene that is to be regulated. For example, the B-PLC promoter sequences (e.g., such as are found in SEQUENCE ID NO: 6) may be disrupted (to decrease B-PLC expression or to abolish a transcriptional control site) or an exogenous promoter (e.g., to increase B-PLC expression) substituted.

The invention also provides methods and reagents for B-PLC Agene knockout≅(i.e., deletion or disruption by homologous recombination of an endogenous B-PLC gene using a recombinantly produced vector). In gene knockout, the targeted sequences can be regulatory sequences (e.g., the B-PLC promoter), or RNA or protein coding sequences. The use of homologous recombination to alter expression of endogenous genes is described in detail in U.S. Pat. No. 5,272,071 (and the U.S. Patents cited supra), WO 91/09955, WO 93/09222, WO 96/29411, WO 95/31560, and WO 91/12650. See also, Moynahan et al., 1996*, Hum. Mol. Genet*. 5:875.

Gene therapy vectors may be introduced into cells or tissues in vivo, in vitro or ex vivo. For ex vivo therapy, vectors may be introduced into cells, e.g., stem cells, taken from the patient and clonally propagated for autologous transplant back into the same patient (see, e.g., U.S. Pat. Nos. 5,399,493 and 5,437,994, the disclosures of which are herein incorporated by reference).

V. Antibodies

The present invention provides antibodies that are specifically immunoreactive with human B-PLC polypeptide. Accordingly, the invention provides or makes use of antibodies that specifically recognize and bind polypeptides which have an amino acid sequence identical, or substantially identical, to the amino acid sequence of SEQ ID NO:2, SEQ ID NO:4, or SEQ ID NO:7 or an immunogenic fragment thereof.

The antibodies of the invention usually exhibit a specific binding affinity for B-PLC of at least about $10^7$, $10^8$, $10^9$, or $10^{10}$ $M^{-1}$.

The anti-B-PLC antibodies of the invention have a variety of uses, e.g., isolation of B-PLC polypeptides (e.g., by immunoaffinity chromatography), detection of B-PLC polypeptides, and for inhibition of B-PLC activity (e.g., in vivo or in vitro).

A. Production of Anti-B-PLC Antibodies

Anti-B-PLC antibodies of the present invention can be made by a variety of means well known to those of skill in the art, e.g., as described supra. As used herein, antibodies are broadly defined and specifically include fragments, chimeras and the like, that specifically binds an B-PLC polypeptide or epitope.

Methods for production of polyclonal or monoclonal antibodies are well known in the art. See, e.g., Coligan, CURRENT PROTOCOLS IN IMMUNOLOGY, Wiley/Greene, N.Y. (1991); Stites et al. (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler and Milstein, *Nature* 256:495–497 (1975) ("Kohler and Milstein"); and Harlow and Lane. These techniques include antibody preparation by selection of antibodies from libraries of recombinant antibodies in phage or similar vectors. See, Huse et al., *Science* 246:1275–1281 (1989) ("Huse"); and Ward et al., *Nature* 341:544–546 (1989).

For production of polyclonal antibodies, an appropriate target immune system is selected, typically a mouse or rabbit, but also including goats, sheep, cows, chickens, guinea pigs, monkeys and rats. The immunoglobulins produced by the host can be precipitated, isolated and purified by routine methods, including affinity purification. Substantially monospecific antibody populations can be produced by chromatographic purification of polyclonal sera.

For monoclonal antibodies, appropriate animals will be selected and the desired immunization protocol followed. The antibodies of the invention may be of any isotype, e.g., IgM, IgD, IgG, IgA, and IgE, with IgG, IgA and IgM most referred. Preferred monoclonal anti-B-PLC antibodies neutralize (i.e., inhibit or block) one or more biological activities of B-PLC. Such antibodies may be obtained by screening hybridoma supernatants for the desired inhibitory activity. Monoclonal antibodies with affinities of $10^8$ liters/mole, preferably $10^9$ to $10^{10}$ or stronger, can be produced by the methods described below. The production of non-human monoclonal antibodies, e.g., murine, lagomorpha, or equine, is well known and can be accomplished by, e.g., immunizing a host animal with a preparation containing B-PLC or fragments thereof. Antibody-producing cells obtained from the immunized animals are immortalized and screened, or screened first for the production of antibody which binds to the B-PLC polypeptide and then immortalized.

Some anti-B-PLC monoclonal antibodies of the present invention are humanized, human or chimeric, in order to reduce their potential antigenicity, without reducing their affinity for their target. Humanized antibodies have been described in the art. See, e.g., Queen, et al., 1989, *Proc. Nat'l Acad. Sci. USA* 86:10029; U.S. Pat. Nos. 5,563,762; 5,693,761; 5,585,089 and 5,530,101. The human antibody sequences used for humanization can be the sequences of naturally occurring human antibodies or can be consensus sequences of several human antibodies. See Kettleborough et al., *Protein Engineering* 4:773 (1991); Kolbinger et al., *Protein Engineering* 6:971 (1993).

Humanized monoclonal antibodies against B-PLC can also be produced using transgenic animals having elements of a human immune system (see, e.g., U.S. Pat. Nos. 5,569,825; 5,545,806; 5,693,762; 5,693,761; and 5,7124,350).

Useful anti-B-PLC binding compositions can also be produced using phage display technology (see, e.g., Dower et al., WO 91/17271 and McCafferty et al., WO 92/01047). In these methods, libraries of phage are produced in which members display different antibodies on their outer surfaces. Antibodies are usually displayed as Fv or Fab fragments. Phage displaying antibodies with a desired specificity are selected by affinity enrichment to an B-PLC polypeptide.

Once expressed, the whole antibodies, their dimers, individual light and heavy chains, or other immunoglobulin forms of the present invention can be purified according to standard procedures of the art, including ammonium sulfate precipitation, affinity chromatography, gel electrophoresis and the like (see generally PROTEIN PURIFICATION: PRINCIPLES AND PRACTICE 3RD EDITION (Springer-Verlag, N.Y., 1994)).

An antibody (e.g. an anti-B-PLC antibody), is substantially pure when at least about 80%, more often at least about 90%, even more often at least about 95%, most often at least about 99% or more of the polypeptide molecules present in a preparation specifically bind the same antigen (e.g., B-PLC polypeptide). For pharmaceutical uses, anti-B-PLC immunoglobulins of at least about 90 to 95% homogeneity are preferred, and 98 to 99% or more homogeneity are most preferred.

B. Modification of B-PLC Antibodies

The antibodies of the present invention can be used with or without modification. Frequently, the antibodies will be labeled by joining, either covalently or non-covalently, a substance which provides for a detectable signal. Such labels include those that are well known in the art, e.g., radioactive, fluorescent, or bioactive (e.g., enzymatic) labels. As labeled binding entities, the antibodies of the invention may be particularly useful in diagnostic applications.

Also encompassed by the invention are hybrid antibodies that share the specificity of antibodies against a B-PLC polypeptide but are also capable of specific binding to a second moiety. In hybrid antibodies, one heavy and light chain pair is from one antibody and the other pair from an antibody raised against another epitope. This results in the property of multi-functional valency, i.e., ability to bind at least two different epitopes simultaneously. Such hybrids can be formed by fusion of hybridomas producing the respective component antibodies, or by recombinant techniques.

VI. Detection and Quantification of B-PLC Polynucleotides and Polypeptides

The present invention provides a number of methods for detection and quantification of B-PLC polypeptides and polynucleotides in biological samples. Altered levels of both B-PLC mRNA and protein can manifest a particular state of disease such as ischemic stroke. The disclosed methods for quantification of B-PLC polynucleotides and polypeptides can be used for diagnostic purposes. Also, any mutations or single nucleotide polymorphisms in the B-PLC gene that may be associated with genetic predispositions to diseases with the B-PLC involvement, can be detected using the methods disclosed herein.

The biological samples can include, but are not limited to, a blood sample, serum, cells (including whole cells, cell fractions, cell extracts, and cultured cells or cell lines), tissues (including tissues obtained by biopsy), body fluids (e.g., urine, sputum, amniotic fluid), or from media (from cultured cells or cell lines), and the like. In one embodiment, the B-PLC polypeptides and polynucleotides are detected in tissue obtained from brain (e.g., human or nonhuman animal brain). In another embodiment, the B-PLC polypeptides and polynucleotides are detected in spleen, where low levels of B-PLC gene are expressed, but where elevated B-PLC levels can be indicative of an neuroinflammatory state of the body.

The methods of detecting or quantifying B-PLC polynucleotides include, but are not limited to, amplification-based assays with or without signal amplification, hybridization based assays, and combination amplification-hybridization assays. For detecting and quantifying B-PLC polypeptides, an exemplary method is an immunoassay that utilizes an antibody or other binding agents that specifically binds to an B-PLC polypeptide or epitope.

A. Assays for B-PLC Polynucleotides

1. Amplification-based Methods

The polymerase chain reaction (PCR), or its variations, is an exemplary amplification-based assay. Examples of techniques sufficient to direct persons of skill through in vitro amplification methods are found in PCR TECHNOLOGY: PRINCIPLES AND APPLICATIONS FOR DNA AMPLIFICATION, H. Erlich, Ed. Freeman Press, New York, N.Y. (1992); PCR PROTOCOLS: A GUIDE TO METHODS AND APPLICATIONS, eds. Innis, Gelfland, Snisky, and White, Academic Press, San Diego, Calif. (1990). Other suitable target amplification methods include the ligase chain reaction (LCR; e.g., Wu and Wallace, 1989, *Genomics* 4:560); strand displacement amplification (SDA; e.g., Walker et al., 1992, *Proc. Natl. Acad. Sci. U.S.A.* 89:392–396); the nucleic acid sequence based amplification (NASBA, Cangene, Mississauga, Ontario; e.g., Compton, 1991, *Nature* 350:91), and the like.

One useful variant of PCR is PCR ELISA (e.g., Boehringer Mannheim Cat. No. 1 636 111) in which digoxigenin-dUTP is incorporated into the PCR product. The PCR reaction mixture is denatured and hybridized with a biotin-labeled oligonucleotide designed to anneal to an internal sequence of the PCR product. The hybridization products are immobilized on streptavidin coated plates and detected using anti-digoxigenin antibodies.

2. Hybridization-based Methods

A variety of methods for specific DNA and RNA measurement using polynucleotide hybridization techniques are known to those of skill in the art (see Sambrook, supra). Hybridization based assays refer to assays in which a polynucleotide probe is hybridized to a target polynucleotide. Usually the polynucleotide hybridization probes of the invention are entirely or substantially identical to a contiguous sequence of the B-PLC nucleic acid sequence. Preferably, polynucleotide probes are at least about 10 bases, often at least about 20 bases, and sometimes at least about 200 bases or more in length. Methods of selecting polynucleotide probe sequences for use in polynucleotide hybridization are discussed in Sambrook, supra.

Polynucleotide hybridization formats are known to those skilled in the art. In some formats, at least one of the target and probe is immobilized. The immobilized polynucleotide may be DNA, RNA, or another oligo- or poly-nucleotide, and may comprise natural or non-naturally occurring nucleotides, nucleotide analogs, or backbones. Such assays may be in any of several formats including: Southern, Northern, dot and slot blots, high-density polynucleotide or oligonucleotide arrays (e.g., GeneChips™ Affymetrix), dip sticks, pins, chips, or beads. All of these techniques are well known in the art and are the basis of many commercially available diagnostic kits. Hybridization techniques are generally described in Hames et al., ed., NUCLEIC ACID HYBRIDIZATION, A PRACTICAL APPROACH IRL Press, (1985); Gall and Pardue *Proc. Natl. Acad. Sci., US.A.*, 63: 378–383 (1969); and John et al., *Nature*, 223: 582–587 (1969).

In one embodiment, in situ hybridization is used to detect B-PLC sequences in a sample. In situ hybridization assays are well known and are generally described in Angerer et al., METHODS ENZYMOL., 152: 649–660 (1987) and Ausubel, supra.

B. B-PLC Polypeptide Assays

In one embodiment, the B-PLC polynucleotide is detected in a sample using an anti-B-PLC antibody of the invention. A number of well established immunological binding assay are suitable for detecting and quantifying B-PLC of the present invention. See, e.g., U.S. Pat. Nos. 4,366,241; 4,376,110; 4,517,288; and 4,837,168, and also METHODS IN CELL BIOLOGY VOLUME 37: ANTIBODIES IN CELL BIOLOGY, Asai, ed. Academic Press, Inc. New York (1993); BASIC AND CLINICAL IMMUNOLOGY 7th Edition, Stites & Terr, eds. (1991); Harlow, supra [e.g., Chapter 14], and Ausubel, supra, [e.g., Chapter 11], each of which is incorporated by reference in its entirety and for all purposes.

Immunoassays for detecting B-PLC may be competitive or noncompetitive. Usually the B-PLC gene product being assayed is detected directly or indirectly using a detectable label. The particular label or detectable group used in the assay is usually not a critical aspect of the invention, so long as it does not significantly interfere with the specific binding of the antibody or antibodies used in the assay. The label may be covalently attached to the capture agent (e.g., an anti-B-PLC antibody), or may be attached to a third moiety, such as another antibody, that specifically binds to the B-PLC polypeptide at a different epitope than recognized by the capture agent.

1. Non-Competitive Immunoassay

Noncompetitive immunoassays are assays in which the amount of captured analyte (here, the B-PLC polypeptide) is directly measured. One such assay is a two-site, monoclonal-based immunoassay utilizing monoclonal antibodies reactive to two non-interfering epitopes on the captured analyte. See, e.g., Maddox et al., 1983*, J. Exp. Med*, 158:1211 for background information. In such an assay, the amount of B-PLC in the sample is directly measured. For example, using a so-called "sandwich" assay, the capture agent (here, the anti-B-PLC antibodies) can be bound directly to a solid substrate where they are immobilized. These immobilized antibodies then capture polypeptide present in the test sample. B-PLC thus immobilized is then bound by a labeling agent, such as a second B-PLC antibody bearing a label. Alternatively, the second B-PLC antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Immunoassay

In competitive assays, the amount of B-PLC polypeptide present in the sample is measured indirectly by measuring the amount of an added (exogenous) B-PLC displaced (or competed away) from a capture agent (e.g., anti-B-PLC antibody) by the analyte present in the sample (e.g., B-PLC polypeptide). In one competitive assay, a known amount of B-PLC is added to the sample and the sample is then contacted with a capture agent (e.g., an anti-B-PLC antibody) that specifically binds to B-PLC. The amount of B-PLC bound to the antibody is inversely proportional to the concentration of B-PLC present in the sample.

Preferably, the antibody is immobilized on a solid substrate. The amount of B-PLC bound to the antibody may be determined either by measuring the amount of B-PLC present in an B-PLC/antibody complex, or alternatively by measuring the amount of remaining uncomplexed B-PLC. The amount of B-PLC may be detected by providing a labeled B-PLC molecule.

For example, using the hapten inhibition assay, the analyte (in this case B-PLC) is immobilized on a solid substrate. A known amount of anti-B-PLC antibody is added to the sample, and the sample is then contacted with the immobilized B-PLC. In this case, the amount of anti-B-PLC antibody bound to the immobilized B-PLC is inversely proportional to the amount of B-PLC present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Other Assays

In addition to the competitive and non-competitive B-PLC polypeptide immunoassays, the present invention also provides other assays for detection and quantification of B-PLC polypeptides. For example, Western blot (immunoblot) analysis can be used to detect and quantify the presence of B-PLC in the sample. The technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the sample with the antibodies that specifically bind B-PLC. The anti-B-PLC antibodies specifically bind to B-PLC on the solid support. These antibodies may be directly labeled or alternatively may be subsequently detected using labeled antibodies (e.g., labeled sheep anti-mouse antibodies) that specifically bind to the anti-B-PLC.

Furthermore, assays such as liposome immunoassays (LIA) are also encompassed by the present invention. LIA utilizes liposomes that is designed to bind specific molecules (e.g., antibodies) and to release encapsulated reagents or markers. The released chemicals are then detected according to standard techniques (see, Monroe et al.,*Amer. Clin. Prod. Rev.* 5:34–41(1986)).

VII. Association of B-PLC Expression and Ishemia

As is apparent from the examples, infra, the reagents disclosed herein find uses in the diagnostic, therapeutic and industrial arts. As shown in the examples, B-PLC expression is induced is induced after damaging ischemia. It will be appreciated that, using detection methods such as those disclosed herein, expression of B-PLC is useful as a diagnostic marker for stroke and other neurological stresses. After ischemia, necrotic and apoptotic cell death occurs that can lead to the release of intracellular proteins (such as B-PLC) or polynucleotides into circulation. Thus, in one embodiment, a test sample (e.g., blood, serum, cerebral-spinal fluid, tissue) from a patient or animal is incubated with an anti-B-PLC antibody of the invention, and the presence or amount of B-PLC is detected.

The amount of B-PLC gene product that is diagnostic of a disease or condition is typically, at least about two, often at least five, frequently at least about ten or about 50 times higher than the levels in cells from tissues (e.g. blood) in a healthy animal or human, and can be easily determined by comparing the expression of the gene in healthy and diseased animals. In some cases, it will be desirable to establish normal or baseline values (or ranges) for gene product expression levels. Normal levels of expression or normal expression products can be determined for any particular population, subpopulation, or group of organisms according to standard methods well known to those of skill in the art and employing the methods and reagents of the invention. Generally, baseline (normal) levels of protein or mRNA are determined by quantitating the amount of protein and/or mRNA in biological samples (e.g., fluids, cells or tissues) obtained from normal (healthy) subjects, e.g., a human subject. For example, normal or control values of protein or mRNA can be determined by quantitating the amount of protein/RNA in a biological sample from the same patient (at different times or stages of progression of a condition) or, from a different individual (e.g., a healthy individual or control animal). In an embodiment, baseline levels are defined from persons of the same or a different age and standard statistical methods used to determination of baseline levels of expression in a healthy population. By comparing the levels of a B-PLC gene product, mutant or variant in the sample with the amount in a healthy cell or tissue of the same type, a different amount of the gene product in the sample as compared to the healthy cell or tissue is prognostic or diagnostic of neurological condition (e.g., a hypoxic-ischemic brain insult such as stroke).

In carrying out the diagnostic and prognostic methods of the invention, it will sometimes be useful to refer to "diagnostic" and "prognostic values." As used herein, "diagnostic value" refers to a value that is determined for the gene product detected in a sample which, when compared to a normal (or "baseline") range of the gene product is indicative of the presence of a disease. "Prognostic value" refers to an amount of the gene product detected in a given cell, tissue, or other biological sample (e.g., blood). The amount (including a zero amount) of the gene product detected in a sample is compared to the prognostic value for the cell such that the relative comparison of the values indicates the presence of disease or the likely outcome of the disease progression. In one embodiment, for example, to assess stroke prognosis, data are collected to obtain a statistically significant correlation of gene product levels with different stroke stages, classes or grades. A predetermined range of expression levels is established for the same cell or tissue sample obtained from subjects having known clinical outcomes. A sufficient number of measurements is made to produce a statistically significant value (or range of values) to which a comparison will be made. The predetermined range of expression levels or activity for a given cell or tissue sample can then be used to determine a value or range for the level of gene product that would correlate to favorable (or less unfavorable) prognosis. The level of gene product from a biological sample (e.g., a patient sample) can then be determined and compared to the low and high ranges and used to predict a clinical outcome. As noted, the effect of therapeutic treatments (e.g., for stroke) can also be monitored by detecting the expression of B-PLC genes or gene products, or there appearance in tissues (e.g., blood) in a patient receiving a treatment for a neurological condition. The restricted tissue expression of B-PLC described infra (FIG. 6) is advantageous in diagnostic and prognostic application, by providing a high degree of specificity and low background.

In one aspect, the invention provides methods for treating a condition characterized by increased B-PLC expression in a mammal, by modulating the activity or expression of B-PLC in a cell or tissue in the mammal. As described herein, the PLC/$IP_3$ regulatory network affects intracellular Ca2+ concentration. Elevated Ca2+ levels have been correlated with apoptotic and necrotic cell death. Thus, in one aspect, B-PLC expression or activity is inhibited to prevent neuronal loss after stroke. The disease states expected to benefit from their treatment with B-PLC agonists or antagonists include those which are associated with rapid changes in intracellular Ca2+ levels and/or in PKC signaling. Examples of conditions that will benefit using the reagents of the invention include acute neurodegenerative conditions such as ischemic stroke, head trauma or injury, as well as neuroinflammatory diseases with consequences to neurons. In a related aspect, the invention provides a method of identifying an agent for treatment or prevention of a hypoxic-ischemic brain insult, by determining whether a compound or treatment is a modulator of activity or expression of a B-PLC.

As described elsewhereherein, the invention also provides assay methods which are capable of screening compounds that modulate the activity, expression, and distribution of the B-PLC genes and proteins disclosed herein.

A variety of assays can be used to evaluate the modulators of B-PLC expression or activity. In one embodiment, the ability of an agent to modulate (e.g., inhibit) binding between a B-PLC polypeptide and $IP_3$ is determined. In one embodiment, the ability of an agent to modulate (e.g., inhibit) phospholipase catalytic activity is determined.

One suitable assay is a cell-based assay. Cells which are stably or transiently transfected with a vector or expression cassette having a nucleic acid sequence encoding a B-PLC protein (e.g., having the sequence of SEQ ID NO:2 or 7, or a varient thereof) are used. In a related embodiment, cells that naturally express B-PLC (e.g., non-recombinant cells) are used, either primary cultures from brain or established cell lines. The cells are maintained under conditions appropriate for expression of the B-PLC polypeptide and are contacted with a putative agent. The lipase activity, IP3-binding activity, or the expression of B-PLC gene products is determined in the presence and absence of the agent.

Optionally, a cellular fraction, such as a membrane fraction, containing the receptor can be used in lieu of whole cells. Alternatively, a property such as a signaling activity, cellular response function and the like is measured in the presence and absence of a test compound, e.g., using recombinant cells expressing a protein of the invention.

In another embodiment, the recombinant B-PLC protein of the invention is expressed, and optionally, purified, and the effect of agents on the biological activity of the protein is assessed. In one embodiment, the protein or fragment is expressed as a fusion protein (e.g., with an epitope tag domain) to facilitate purification and to provide other advantages.

Several methods of automating assays have been developed in recent years so as to permit screening of tens of thousands of compounds in a short period. See, e.g., Fodor et al., 1991, *Science* 251: 767–73.

Assays for catalytic activity can be carried out using routine methods known in the art, e.g., see references listed supra. Similarly, assays for binding between B-PLC and IP3 can be carried out using routine methods known in the art, e.g. as described herein.

Thus, in an embodiment, the invention provides a method of identifying an agent that modulates of B-PLC activity by contacting a cell or composition comprising a B-PLC protein and detecting a difference in protein activity in the presence of the agent compared to the absence of the agent. In an embodiment, the B-PLC polypeptide is encoded by a polynucleotide with the sequence of SEQ. ID. NO:1, or a polynucleotide that hybridizes under stringent conditions to SEQ. ID. NO:1. In an embodiment the polypeptide has the sequence of SEQ ID NO:2 or a conservatively substituted variant thereof. in one embodiment, the difference in protein activity is a difference in binding of $IP_3$.

In a related embodiment, the invention provides a method of identifying an agent that modulates of B-PLC expression comprising contacting a cell that expresses the B-PLC protein of SEQ ID NO:2 or NO:7 or a naturally occurring allele thereof, and detecting a change in B-PLC expression in the presence of the agent compared to the absence of the agent. In an embodiment, the cell is a cell in a non-human animal.

VIII. Pharmaceutical Compositions

The present invention further provides therapeutic compositions comprising agonists, antagonists, or targets of B-PLC and methods of treating physiologic or pathologic conditions mediated by B-PLC, in particular neurological conditions such as ischemic stroke.

B-PLC polypeptides, fragments thereof, sense and antisense polypeptides, anti-B-PLC antibodies or binding fragments thereof, and antagonists or agonists of B-PLC activity, can be directly administered under sterile conditions to the host to be treated. However, while it is possible for the active ingredient to be administered alone, it is often preferable to present it as a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the patient. For example, the bioactive agent can be complexed with carrier proteins such as ovalbumin or serum albumin prior to their administration in order to enhance stability or pharmacological properties such as half-life. Furthermore, therapeutic formulations of this invention can be combined with or used in association with other chemotherapeutic or chemopreventive agents.

Therapeutic formulation containing known PLC inhibitors such as U73122, manoalide (Bennett CF, et al. Mol Pharmacol. 1987 (32) 587–93) or derivatives thereof may be used to attenuate excessive B-PLC activity in conditions described supra.

Therapeutic formulations can be prepared by any methods well known in the art of pharmacy. See, e.g., Gilman et al (eds.) (1990) Goodman and Gilman's: The Pharmacological Bases of Therapeutics (8th ed.) Pergamon Press; and (1990) Remington's Pharmaceutical Sciences (17th ed.) Mack Publishing Co., Easton, Pa.; Avis et al (eds.) (1993) Pharmaceutical Dosage Forms: Parenteral Medications Dekker, N.Y.; Lieberman et al. (eds.) (1990) Pharmaceutical Dosage Forms: Tablets Dekker, N.Y.; and Lieberman et al (eds.) (1990) Pharmaceutical Dosage Forms: Disperse Systems Dekker, N.Y.

The therapeutic formulations can conveniently be presented in unit dosage form and administered in a suitable therapeutic dose. A suitable therapeutic dose can be determined by any of the well known methods such as clinical studies on mammalian species to determine maximum tolerable dose and on normal human subjects to determine safe dosage.

The therapeutic formulations can be delivered by any effective means which could be used for treatment. These means include but are not limited to oral, rectal, nasal, pulmonary administration, or parenteral (including subcutaneous, intramuscular, intravenous and intradermal) infusion into the bloodstream.

IX. Kits

Reagents useful for the therapeutic and diagnostic (detection) methods of the invention are conveniently provided in kit form. Thus, the present invention encompasses kits that contain polypeptides, antibodies, and polynucleotides of the present invention.

In one embodiment, the kit comprises one or more of the following in a container: (1) B-PLC polynucleotides (e.g., oligonucleotide primers or probes corresponding to the B-PLC cDNA sequence and capable of amplifying the target polynucleotides); (2) anti-B-PLC antibodies; (3) B-PLC polypeptides or fragments, optionally coated on a solid surface (such as a slide, multiple well plate, or test tube) (4) a B-PLC polynucleotide (e.g., for use as positive controls in assays), (5) and tubes. Instructions for carrying out the detection methods of the invention, and calibration curves can also be included.

X. EST Sequences

The ESTs (and corresponding clones) listed below have sequence similarity to a human or rodent B-PLC of the invention. In some embodiments the polynucleotide or polypeptides fragments are contemplated to be other than one or more of the molecules listed in Table 2 or translation products thereof. However, inclusion in Table 2 should not be construed as an indication that any sequence or polynucleotide is prior art.

TABLE 2

| |
|---|
| 1) gb\|AW408450.1\|AW408450 UI-HF-BK0-abm-c-02-0-UI.r1 NIH_MGC_36 *Homo sapiens* cDNA clone IMAGE:3056642 5' Length = 455 |
| 2) gb\|AA277075.1\|AA277075 vc06e01.r1 *Mus musculus* cDNA clone IMAGE:765720 5'; Length = 517 |
| 3) gb\|AA772973.1\|AA772973 af33h09.s1 *Homo sapiens* cDNA clone IMAGE:1033505 3'; Length = 471 |

TABLE 2-continued

| |
|---|
| 4) gb\|AW493796.1\|AW493796 UI-M-BH3-aug-c-08-0-UI.s1 NIH_BMAP_M_S4 *Mus musculus* cDNA clone UI-M-BH3-aug-c-08-0-UI 3' Length = 436 |
| 5) gb\|AW500653.1\|AW500653 UI-HF-BN0-akk-h-02-0-UI.r1 NIH_MGC_50 *Homo sapiens* cDNA clone IMAGE:3077595 5' Length = 434 |
| 6) gb\|BE655266.1\|BE655266 UI-M-BG1-aij-g-02-0-UI.r1 NIH_BMAP_MSC_N *Mus musculus* cDNA clone UI-M-BG1-aij-g-02-0-UI 5' Length = 390 |
| 7) gb\|AA690679.1\|AA690679 vu53h08.r1 *Mus musculus* cDNA clone IMAGE:1195167 5; Length = 484 |
| 8) emb\|AL024179.1\|AL024179 k8311b43 *Mus musculus* cDNA clone 528-6E13 5' Length = 366 |
| 9) gb\|AW478640.1\|AW478640 21359 MARC 1BOV *Bos taurus* cDNA 5' Length = 345 |
| 10) gb\|T78839.1\|T78839 yc96g09.r1 *Homo sapiens* cDNA clone IMAGE:23861 5' Length = 553 |
| 11) gb\|AW428387.1\|AW428387 66309 MARC 4BOV *Bos taurus* cDNA 5' Length = 312 |
| 12) gb\|AW466123.1\|AW466123 BP230021B20H7 *Bos taurus* cDNA clone BP230021B20H7 5' Length = 549 |

XI. EXAMPLES

The following examples are provided to further illustrate the present invention. They are not included to limit the invention in any way.

Example 1

Isolation of Rat B-PLC Polynucleotide

The B-PLC cDNA was identified among the sequences comprising the library of genes upregulated during ischemic preconditioning in the rat hippocampal tissue. Rats of the same strain, age and sex were divided into two experimental groups: a.) animals in the first group underwent surgery including a single 3 minute bilateral occlusion of the carotid arteries ("experimental group") and b.) animals in the second group were sham operated ("control group"). The animals were sacrificed 4 hours after the operation and the CA1 and CA3 regions of their hippocampi were dissected. Poly-A+RNA prepared from the collected tissues was converted in double-stranded cDNA (dscDNA). Subtractive hybridization was carried out using the dscDNA from preconditioned animals with an excess of dscDNA prepared from the sham operated animals. Differentially expressed gene fragments were cloned into a plasmid vector, and the resulting library was transformed in *E. coli* cells.

Inserts of recombinant clones were amplified by the polymerase chain reaction (PCR). The PCR products (fragments of 200–2,000 bp in size) were sequenced using an oligonucleotide complementary to common vector sequences. The resulting sequence information was compared to public databases using the BLAST (blastn and tblastx) algorithm and determined to have similarity to phospholipase-encoding sequences.

Nucleotide sequences of genes upregulated in the rat hippocampus upon ischemic preconditioning were analyzed by the BLAST software to identify the relationship of the isolated genes to those available in the GENBANK.

Example 2

Isolation of Human B-PLC Polynucleotide

A partial rat cDNA clone encoding a novel PLC, SEQ ID NO:3 (see FIG. 3), was obtained as described in Example 1. The rat clone was used to screen human hippocampal and fetal brain cDNA libraries in the lambda phage vector to isolate the full-length human PLC cDNA. A radioactively labeled DNA fragment corresponding to SEQ ID NO:3 was hybridized under low stringency (hybridization in 5×SSC/50% formamide at 42C for 16 h, and wash in 0.1×SSC/0.1% SDS at 50C for 30 min.) to human cDNA libraries immobilized to membrane filters. Positive, hybridizing human cDNA clones were isolated and sequenced. At least 20 different hybridizing clones were isolated from both libraries. Lambda DNA from all clones was isolated and mapped by restriction digests. The longest overlapping clones were used to deduce the nucleotide sequence encoding the B-PLC protein.

Example 3

Tissue-Specific Expression of human B-PLC mRNA

The expression pattern of B-PLC was determined by Northern blotting. mRNA was isolated using standard methods (Sambrook et al., supra) from the following rat organs: brain, heart, lung, liver, kidney, spleen, thymus, testis, adrenal glands. mRNAs were separated by gel electrophoresis and blotted to nylon membrane filter (Sambrook). The membranes were prehybridized in 7% SDS, 0.5 M NaHPO4, 1 mM EDTA at 65° C. for 15 minutes. Using fresh prehybridization solution, the membranes were hybridized with the labeled probe for 18 hours. The hybridized membranes were briefly rinsed in 5% SDS, 40 mM NaHPO4, 1 mM EDTA and then washed for 45 minutes at 65° C. with fresh solution. This wash solution was replaced with 1% SDS, 40 mM NaHPO4, 1 mM EDTA and washed twice for 45 minutes at 65° C. with fresh solution. After washing, the membranes were sandwiched between plastic wrap and exposed overnight to Kodak X-OMAT AR film with a Dupont Lightening Plus intensifying screen at −70° C.

The results are shown in FIG. 6. Numbers in boxes indicate sizes of RNA size standards. The size of the predominant B-PLC mRNA is 5 kb. An additional transcript of about 3.5 kb can be detected in brain mRNA, and may indicate the presence of a splice variant of B-PLC in that tissue.

Example 4

In Situ Hybridization of B-PLC Probe to Rat Brain

Figure 7:
FIG. 7 shows the result of in situ hybridization of a B-PLC probe to rat brain. In situ hybridization of brain slices from control rats (upper left panel) and rats undergone ischemic preconditioning (3 min global ischemic pulse) (lower left panel), damaging ischemic pulse (10 min global ischemia) (upper right panel) and ischemic damage preceded by ischemic preconditioning (lower right panel). Note the higher intensity of the signal in the hippocampal region (arrow) in upper right panel (damaging ischemia).

The distribution of the B-PLC mRNA in the rat brain was determined by in situ hybridization. Thin brain slices were cut from control rat brains and from brains of rats that had received 3 min global ischemic pulse (ischemic preconditioning), 10 min global ischemia (damaging ischemia) or ischemic preconditioning 48 h prior to damaging ischemia. An antisense oligo complementary to the rat B-PLC mRNA (having the sequence 5'-AGGATTCTCATTGGCGTATTTACTGGCTAGCACT TCATTG-3') (SEQ ID NO: 22) was radioactively labeled with $^{35}S$ and allowed to hybridize to the brain slices according to a standard protocol (Wisden, W. & Morris, B. J. in In Situ Hybridization Protocols for the Brain (ed. Wisden, W. & Morris, B. J.), Academia, London, 1994, 9–30). Signal from the specifically bound oligonucleotides was detected after several weeks exposure to Kodak BIOMAX film at −70° C. The expression of B-PLC could be observed in all major brain areas such as cerebral cortex and hippocampus (see FIG. 7). Furthermore, a significant upregulation of the B-PLC mRNA was detectable in cortex and hippocampus in rat brain slices that had received global ischemia for 10 min.

All references cited herein are incorporated herein by reference in their entirety and for all purposes to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method for the diagnosis of a neurological condition in an animal, comprising (a) obtaining a biological sample from the animal; and (b) detecting an increased level of B-PLC comprising the polypeptide of SEQ ID NO:7 in the sample compared to the level in a healthy animal, wherein said increased level is diagnostic of a neurological condition in the animal.

2. The method of claim 1, wherein the biological sample is blood.

3. The method of claim 1, wherein the increased level of B-PLC is detected using an immunoassay.

4. The method of claim 1, wherein the neurological condition is hypoxic-ischemic brain insult or a neuroinflammatory disease.

5. The method of claim 4, wherein the neurological condition is hypoxic-ischemic brain insult which is a stroke.

6. A method for the diagnosis of a neurological condition in an animal, comprising (a) obtaining a biological sample from the animal; and (b) detecting an increased level of B-PLC in the sample compared to the level in a healthy animal by using an antibody that specifically binds the polypeptide of SEQ ID NO:7, wherein said increased level is diagnostic of a neurological condition in the animal.

* * * * *

SEQUENCE LISTING

```
<160> NUMBER OF SEQ ID NOS: 22

<210> SEQ ID NO 1
<211> LENGTH: 3006
<212> TYPE: DNA
<213> ORGANISM: Homo sapiens

<400> SEQUENCE: 1

atgccaacag agaagaagat cagcagtgca agtgattgta ttaattcaat ggttgagggt     60

tcagaactca aaaaggttcg ctccaactct agaatttatc ataggtactt tctactggat    120

gctgacatgc agagcctaag gtgggagcca tctaagaagg attctgagaa agccaagatt    180

gacattaaat ccatcaagga agtgagaacg ggaaaaaaca cagacatatt ccgcagcaat    240

ggcatttctg accagatatc tgaagattgt gcgttttccg tcatatatgg agagaattat    300

gagtcactgg atttggttgc cactctcgca gatgttgcaa acatctgggt tacaggactg    360

cggtacctaa tttcttatgg aaaacataca cttgatatgt tagaaagtag ccaagataac    420

atgaggactt cttgggtttc acaaatgttt agtgaaattg atgtagataa ccttggacat    480

ataactctgt gtaatgctgt gcaatgtatc agaaacctca atcctggttt aaaaacgagc    540

aaaattgagc ttaagttcaa agaattgcat aaatcaaagg acaaagctgg taccgaggtc    600

acaaaggaag aatttattga ggtttttcat gagctttgta ctagacctga aatttatttc    660

cttttagttc agttttcaag caataaagaa ttccttgata ccaaggacct tatgatgttt    720

cttgaggcag aacagggtgt ggcacatata aatgaggaaa taagccttga aattattcac    780

aaatatgaac catccaaaga gggtcaggaa aagggctggc tctccataga cgggttcact    840

aattacctta tgtcacctga ctgttatata ttcgatccag aacataagaa ggtctgtcag    900

gatatgaagc aacctctgtc tcattacttt ataaactcat ctcataatac atacttaata    960

gaggatcagt tccgaggtcc ctccgacatc acaggatata ttcgagctct taaaatgggt   1020

tgccggagtg ttgaattaga tgtatgggat gggccggaca atgaacctgt aatttacaca   1080

ggccacacca tgacctctca gatagttttc cgcagtgtca ttgatattat taacaagtat   1140

gcattctttg cttcagagta tcctcttatc ttgtgtttag aaaaccactg ttccattaaa   1200

caacagaagg taatggttca gcacatgaag aaacttttag gagacaagct ctatacaaca   1260

tcacccaatg ttgaggaatc ttatctacca tccccagatg tcctgaaagg gaaaatacta   1320

attaaagcaa agaagctgtc ctcaaattgt tctggggtag aaggagatgt tactgacgaa   1380

gatgaaggag cagaaatgtc tcagaggatg ggaaaagaga acatggagca acccaataat   1440
```

-continued

```
gtgcctgtga agcgatttca gctttgtaaa gaactgtctg aactggtcag catctgcaaa   1500

tcagttcagt tcaaagaatt tcaggtgtcg tttcaggttc agaagtactg ggaagtctgt   1560

tcctttaatg aagtgcttgc cagcaagtac gccaatgaaa atccagggga ctttgtaaat   1620

tacaacaaac gttttcttgc tagggttttt cccagtccaa tgagaattga ttccagtaac   1680

atgaatcctc aagatttttg gaaatgtggt tgccaaattg tagccatgaa ctttcagaca   1740

ccaggactga tgatggacct gaatattggc tggtttaggc agaacggaaa ctgtggctat   1800

gtcctccggc cagccatcat gagggaggag gtctccttct tcagcgccaa tacaaaagac   1860

tctgtcccag ggtctcacc tcaacttctt cacattaaaa tcatcagtgg gcagaacttt   1920

cccaagccca aaggatcagg tgccaaaggt gatgtggtag atccttatgt ctatgttgaa   1980

atccatggaa tccctgctga ttgtgcagaa caaaggacaa aaacagtgca ccagaatgga   2040

gacgctccca tttttgatga aagctttgaa tttcaaatca acctgcctga actggccatg   2100

gtgcgctttg tagtgctgga tgatgactac attggggatg aattcatggg ccagtacaca   2160

attccctttg aatgtttaca gacgggctac cgccatgtcc ccctgcagtc cttaactgga   2220

gaggtccttg cacatgcttc tttatttgtc cacgtggcta ttactaaccg aagagtagga   2280

ggaaagcctc ataaaagggg cctttctgtg agaaaaggga agaaatccag ggaatatgca   2340

tctttgagaa cactgtggat taaaaccgtg gatgaggtat tcaagaatgc ccagcccccct   2400

atacgggatg ccacagatct gagagaaaac atgcagaatg cggtggtgtc attcaaggag   2460

ctgtgtggcc tctcctctgt ggccaatctc atgcagtgca tgttggcggt gtctccccgc   2520

tttctggggc ccgataacac accccctagtg gtcctaaatc tcagcgagca gtaccccaca   2580

atggagctgc agggaattgt gtcggaggtt ctgaagaaga tcgtaacaac ttatgacatg   2640

atgattcagt ccctcaaggc gttgattgaa aatgcagatg ctgtatatga aaagatcgta   2700

cattgtcaga aggcagccat ggaattccat gaacacttgc acagcatagg caccaaggaa   2760

ggtttgaagg aaagaaaact acaaaaagca gtggagagct ttacctggaa tattaccatc   2820

ttaaagggac aagcagatct tttgaaatat gctaagaatg agacattgga gaacctgaaa   2880

caaatccatt ttgctgctgt ttcatgtgga ctgaataaac caggcaccga aaatgctgat   2940

gtccagaagc cacgccggag cttggaagtc atacccgaaa aagcaaacga tgaaactgga   3000

gaatga                                                               3006
```

<210> SEQ ID NO 2
<211> LENGTH: 1001
<212> TYPE: PRT
<213> ORGANISM: Homo sapiens

<400> SEQUENCE: 2

```
Met Pro Thr Glu Lys Lys Ile Ser Ser Ala Ser Asp Cys Ile Asn Ser
  1               5                  10                  15

Met Val Glu Gly Ser Glu Leu Lys Lys Val Arg Ser Asn Ser Arg Ile
             20                  25                  30

Tyr His Arg Tyr Phe Leu Leu Asp Ala Asp Met Gln Ser Leu Arg Trp
         35                  40                  45

Glu Pro Ser Lys Lys Asp Ser Glu Lys Ala Lys Ile Asp Ile Lys Ser
     50                  55                  60

Ile Lys Glu Val Arg Thr Gly Lys Asn Thr Asp Ile Phe Arg Ser Asn
 65                  70                  75                  80

Gly Ile Ser Asp Gln Ile Ser Glu Asp Cys Ala Phe Ser Val Ile Tyr
```

-continued

```
                85                  90                  95

Gly Glu Asn Tyr Glu Ser Leu Asp Leu Val Ala Thr Leu Ala Asp Val
            100                 105                 110

Ala Asn Ile Trp Val Thr Gly Leu Arg Tyr Leu Ile Ser Tyr Gly Lys
        115                 120                 125

His Thr Leu Asp Met Leu Glu Ser Ser Gln Asp Asn Met Arg Thr Ser
    130                 135                 140

Trp Val Ser Gln Met Phe Ser Glu Ile Asp Val Asp Asn Leu Gly His
145                 150                 155                 160

Ile Thr Leu Cys Asn Ala Val Gln Cys Ile Arg Asn Leu Asn Pro Gly
                165                 170                 175

Leu Lys Thr Ser Lys Ile Glu Leu Lys Phe Lys Glu Leu His Lys Ser
            180                 185                 190

Lys Asp Lys Ala Gly Thr Glu Val Thr Lys Glu Glu Phe Ile Glu Val
        195                 200                 205

Phe His Glu Leu Cys Thr Arg Pro Glu Ile Tyr Phe Leu Leu Val Gln
    210                 215                 220

Phe Ser Ser Asn Lys Glu Phe Leu Asp Thr Lys Asp Leu Met Met Phe
225                 230                 235                 240

Leu Glu Ala Glu Gln Gly Val Ala His Ile Asn Glu Glu Ile Ser Leu
                245                 250                 255

Glu Ile Ile His Lys Tyr Glu Pro Ser Lys Glu Gly Gln Glu Lys Gly
            260                 265                 270

Trp Leu Ser Ile Asp Gly Phe Thr Asn Tyr Leu Met Ser Pro Asp Cys
        275                 280                 285

Tyr Ile Phe Asp Pro Glu His Lys Lys Val Cys Gln Asp Met Lys Gln
    290                 295                 300

Pro Leu Ser His Tyr Phe Ile Asn Ser Ser His Asn Thr Tyr Leu Ile
305                 310                 315                 320

Glu Asp Gln Phe Arg Gly Pro Ser Asp Ile Thr Gly Tyr Ile Arg Ala
                325                 330                 335

Leu Lys Met Gly Cys Arg Ser Val Glu Leu Asp Val Trp Asp Gly Pro
            340                 345                 350

Asp Asn Glu Pro Val Ile Tyr Thr Gly His Thr Met Thr Ser Gln Ile
        355                 360                 365

Val Phe Arg Ser Val Ile Asp Ile Ile Asn Lys Tyr Ala Phe Phe Ala
    370                 375                 380

Ser Glu Tyr Pro Leu Ile Leu Cys Leu Glu Asn His Cys Ser Ile Lys
385                 390                 395                 400

Gln Gln Lys Val Met Val Gln His Met Lys Lys Leu Leu Gly Asp Lys
                405                 410                 415

Leu Tyr Thr Thr Ser Pro Asn Val Glu Glu Ser Tyr Leu Pro Ser Pro
            420                 425                 430

Asp Val Leu Lys Gly Lys Ile Leu Ile Lys Ala Lys Lys Leu Ser Ser
        435                 440                 445

Asn Cys Ser Gly Val Glu Gly Asp Val Thr Asp Glu Asp Glu Gly Ala
    450                 455                 460

Glu Met Ser Gln Arg Met Gly Lys Glu Asn Met Glu Gln Pro Asn Asn
465                 470                 475                 480

Val Pro Val Lys Arg Phe Gln Leu Cys Lys Glu Leu Ser Glu Leu Val
                485                 490                 495

Ser Ile Cys Lys Ser Val Gln Phe Lys Glu Phe Gln Val Ser Phe Gln
            500                 505                 510
```

-continued

```
Val Gln Lys Tyr Trp Glu Val Cys Ser Phe Asn Glu Val Leu Ala Ser
        515                 520                 525

Lys Tyr Ala Asn Glu Asn Pro Gly Asp Phe Val Asn Tyr Asn Lys Arg
    530                 535                 540

Phe Leu Ala Arg Val Phe Pro Ser Pro Met Arg Ile Asp Ser Ser Asn
545                 550                 555                 560

Met Asn Pro Gln Asp Phe Trp Lys Cys Gly Cys Gln Ile Val Ala Met
                565                 570                 575

Asn Phe Gln Thr Pro Gly Leu Met Met Asp Leu Asn Ile Gly Trp Phe
            580                 585                 590

Arg Gln Asn Gly Asn Cys Gly Tyr Val Leu Arg Pro Ala Ile Met Arg
        595                 600                 605

Glu Glu Val Ser Phe Phe Ser Ala Asn Thr Lys Asp Ser Val Pro Gly
    610                 615                 620

Val Ser Pro Gln Leu Leu His Ile Lys Ile Ile Ser Gly Gln Asn Phe
625                 630                 635                 640

Pro Lys Pro Lys Gly Ser Gly Ala Lys Gly Asp Val Val Asp Pro Tyr
                645                 650                 655

Val Tyr Val Glu Ile His Gly Ile Pro Ala Asp Cys Ala Glu Gln Arg
            660                 665                 670

Thr Lys Thr Val His Gln Asn Gly Asp Ala Pro Ile Phe Asp Glu Ser
        675                 680                 685

Phe Glu Phe Gln Ile Asn Leu Pro Glu Leu Ala Met Val Arg Phe Val
    690                 695                 700

Val Leu Asp Asp Asp Tyr Ile Gly Asp Glu Phe Met Gly Gln Tyr Thr
705                 710                 715                 720

Ile Pro Phe Glu Cys Leu Gln Thr Gly Tyr Arg His Val Pro Leu Gln
                725                 730                 735

Ser Leu Thr Gly Glu Val Leu Ala His Ala Ser Leu Phe Val His Val
            740                 745                 750

Ala Ile Thr Asn Arg Arg Val Gly Gly Lys Pro His Lys Arg Gly Leu
        755                 760                 765

Ser Val Arg Lys Gly Lys Lys Ser Arg Glu Tyr Ala Ser Leu Arg Thr
    770                 775                 780

Leu Trp Ile Lys Thr Val Asp Glu Val Phe Lys Asn Ala Gln Pro Pro
785                 790                 795                 800

Ile Arg Asp Ala Thr Asp Leu Arg Glu Asn Met Gln Asn Ala Val Val
                805                 810                 815

Ser Phe Lys Glu Leu Cys Gly Leu Ser Ser Val Ala Asn Leu Met Gln
            820                 825                 830

Cys Met Leu Ala Val Ser Pro Arg Phe Leu Gly Pro Asp Asn Thr Pro
        835                 840                 845

Leu Val Val Leu Asn Leu Ser Glu Gln Tyr Pro Thr Met Glu Leu Gln
    850                 855                 860

Gly Ile Val Ser Glu Val Leu Lys Lys Ile Val Thr Thr Tyr Asp Met
865                 870                 875                 880

Met Ile Gln Ser Leu Lys Ala Leu Ile Glu Asn Ala Asp Ala Val Tyr
                885                 890                 895

Glu Lys Ile Val His Cys Gln Lys Ala Ala Met Glu Phe His Glu His
            900                 905                 910

Leu His Ser Ile Gly Thr Lys Glu Gly Leu Lys Glu Arg Lys Leu Gln
        915                 920                 925
```

-continued

```
Lys Ala Val Glu Ser Phe Thr Trp Asn Ile Thr Ile Leu Lys Gly Gln
    930                 935                 940

Ala Asp Leu Leu Lys Tyr Ala Lys Asn Glu Thr Leu Glu Asn Leu Lys
945                 950                 955                 960

Gln Ile His Phe Ala Ala Val Ser Cys Gly Leu Asn Lys Pro Gly Thr
                965                 970                 975

Glu Asn Ala Asp Val Gln Lys Pro Arg Arg Ser Leu Glu Val Ile Pro
            980                 985                 990

Glu Lys Ala Asn Asp Glu Thr Gly Glu
        995                 1000
```

<210> SEQ ID NO 3
<211> LENGTH: 598
<212> TYPE: DNA
<213> ORGANISM: Rattus sp.

<400> SEQUENCE: 3

```
tgttattaat aaaaataaag ggccagaatt gtctcaaagg atgggaaaag agattgggac     60

caccccaccc atgggcttgt aaagcgattt aagctttgca aagacctgtc ttaaactggc    120

agcatctgta agtcagtcca gttcaagaag ttccaggtgt cgtttcaggt gcaaaagtac    180

tgggaagtgt gttcattcaa tgaagtgcta gccagtaaat acgccaatga gaatcctggg    240

gactttgtaa attacaataa gcgtttcctc gccagagtct ttcctagtcc aatgagaatt    300

gattctagta acatgaaccc tcaagatttt tggaaatgtg gctgtcaaat cgtagccatg    360

aactttcaga ctccagggct aatgatggat ctgaacattg gctggtttag gcagaatgga    420

aactgtggct atgttcttcg accagccatc atgagggaag aagtctcctt cttcagtgcc    480

aacacaaagg actctgtccc tggagtttcg cctcagttgc ttcacatcaa aatcatcagt    540

ggccagaact ttcccaagcc caaagggtca ggtgccaaag gggatgtggt ggaccctt      598
```

<210> SEQ ID NO 4
<211> LENGTH: 161
<212> TYPE: PRT
<213> ORGANISM: Rattus sp.

<400> SEQUENCE: 4

```
Thr Gly Ser Ile Cys Lys Ser Val Gln Phe Lys Lys Phe Gln Val Ser
  1               5                  10                  15

Phe Gln Val Gln Lys Tyr Trp Glu Val Cys Ser Phe Asn Glu Val Leu
            20                  25                  30

Ala Ser Lys Tyr Ala Asn Glu Asn Pro Gly Asp Phe Val Asn Tyr Asn
        35                  40                  45

Lys Arg Phe Leu Ala Arg Val Phe Pro Ser Pro Met Arg Ile Asp Ser
     50                  55                  60

Ser Asn Met Asn Pro Gln Asp Phe Trp Lys Cys Gly Cys Gln Ile Val
 65                  70                  75                  80

Ala Met Asn Phe Gln Thr Pro Gly Leu Met Met Asp Leu Asn Ile Gly
                 85                  90                  95

Trp Phe Arg Gln Asn Gly Asn Cys Gly Tyr Val Leu Arg Pro Ala Ile
            100                 105                 110

Met Arg Glu Glu Val Ser Phe Phe Ser Ala Asn Thr Asp Lys Ser Val
        115                 120                 125

Pro Gly Val Ser Pro Gln Leu Leu His Ile Lys Ile Ile Ser Gly Gln
    130                 135                 140

Asn Phe Pro Lys Pro Lys Gly Ser Gly Ala Lys Gly Asp Val Val Asp
```

-continued 145 150 155 160

Pro

<210> SEQ ID NO 5
<211> LENGTH: 2958
<212> TYPE: DNA
<213> ORGANISM: Rattus sp.

<400> SEQUENCE: 5
gagcaaaccc cacggcctgc cccgccggag caccatcatc aacgatggca cgaagcagaa 60
aagagagcgg aagaagaccg tgtcattcag cagcatgcca acagagaaga agatcagcag 120
tgcaagcgac tgcatcaact caatggtgga gggctctgaa ctcaagaagg ttcgttcaaa 180
ctccagaatt taccatcggt actttctgct ggacgccgac atgcaaagcc tgaggtggga 240
gccatccaag aaggattctg agaaagccaa gattgacatc aagtccatca aggaagttag 300
aacggggaaa aacacagata tattcccgca gcaatgggca tttctgagca aatatctgaa 360
agattgtgcg ttttcagtca tatatggaga aaatatgagt cactccgatt tggttgccaa 420
ttctgcagat gttgcaaaca tctgggtgac aggactccgg tacctgattt cttatgggaa 480
acatacactt gatatgttag aaagtagcca agacaacatg aggacttgtt gggtttcaca 540
gatgtttagt gaaattgatg tagatgacct tggacatata actctgtgta atgctgttca 600
gtgtatcaga aacctcaatc ctggcttaaa aacaagcaaa attgagctta agttcaaaga 660
actgcataaa tcaaaggaca aaactggtac tgaaatcaca aaggaagaat ttgttgaggt 720
ttttcatgaa ctttgcacta gacctgaaat ttacttcctt ttagttcagt tttcaagcaa 780
taaagaattc cttgatacca aggaccttat gatgtttctt gaggcagaac agggtgtagc 840
acatataaat gaggaaataa gcctggaaat tattcacaaa tatgagccat ccaaagaagg 900
ccaggaaaag ggctggctct ccatagatgg gttcactaat tacctgatgt cacctgattg 960
ttacatcttt gatccggaac ataagaaggt ctgtcaggat atgaagcaac ctctgtctca 1020
ttacttcata aactcatctc ataatacata cttaatagag gaccagttcc cgggtccctc 1080
tgacattaca ggatatatcc gtgctcttaa aatgggttgc aggagtgttg agttggatgt 1140
gtgggatggg ccagataatg agcccgtgat ttacacaggc cacaccatga cctctcagat 1200
agtcttccgc agtgtcatcg atatcattaa caagtatgca ttctttgctt ctgagtatcc 1260
tctcatcctg tgtttagaaa atcattgttc tattaaacaa caaaaggtga tggttcaaca 1320
catgaagaaa attttaggag acaagctgta taccacatca cccaacatgg aggaatctta 1380
tctaccatcc cccgatgtcc tgaaagggaa aatactaatc aaagcaaaga agctgtcttc 1440
aaattgctct ggtgtggaag gggatgttac tgatgaagat gaaggggcag aaatgtctca 1500
gaggatgggg aaagagaatg tggaacaacc caaccatgtg cctgtgaagc gatttcagct 1560
ttgcaaagac ctgtctgaac tggtcagcat ctgtaagtca gtccagttca aggagttcca 1620
ggtgtcgttt caggtgcaga agtactggga agtgtgttca ttcaatgaag tgctagccag 1680
taaatacgcc aatgagaatc ctggggactt tgtaaattac aataagcgtt tcctcgccag 1740
agtctttcct agtccaatga gaattgattc tagtaacatg aaccctcaag atttttggaa 1800
atgtggctgt caaatcgtag ccatgaactt tcagactcca gggctaatga tggatctgaa 1860
cattggctgg tttaggcaga atggaaactg ggcgctagtt cttcgaccag ccatcatgag 1920
ggaagaagtc tccttcttca gtgccaacac aaaggactct gtccctggag tttcgcctca 1980
gttgcttcac atcaaaatca tcagtggcca gaactttccc aagcccaaag ggtcaggtgc 2040

-continued

```
caaaggggat gtggtggacc cttatgtcta tgtggaaatc catggcattc ctgctgactg   2100
cgcagaacag aggacgaaaa ctgtgaacca gaatggagat gctcctatgt ttgatgaaag   2160
ctttgaattt caaatcaacc tccccgaact agccatggtg cgctttgtag tgctggatga   2220
tgactacatt ggcgatgaat ttattggcca gtacacgatt ccctttgaat gtttacaaac   2280
gggctaccgc catgtgcctc tgcagtcctt gactggagag gtccttgccc atgcttctct   2340
gttcgtccac gtggctatta ctaacagaag aggaggaggg aagcctcata aacggggcct   2400
ttctgtgagg aaagggaaga agtcccggga atatgcatct ctgagaacac tgtggattaa   2460
aactgtagat gaggtgttca agaatgccca gccccccatc cgggatgcca cagacctgag   2520
agagaacatg cagaatgcag tggtttcttt caaggaatta tgtggcctct cctcagtggc   2580
caaccttatg cagtgcatgc tggccgtgtc tcctcgattc ctggggcctg acaatactcc   2640
cctggtggtc ttgaatctta gtgagcccta ccccaccatg gaactgcagg ccatcgtgcc   2700
tgaggttctg aagaagatcg tcacaactta tgacatgatg attcagtccc tcaaggcacg   2760
attgaaaatg cagatgctgt gtatgaaaag attgtgcact gtcagaaggc agccatggaa   2820
tttcatgaac acttgcacag cataggcacc aaggagggac tgaaggaacg gaaactacag   2880
aaggcggtgg agagctttac ctggaatatt acgattttaa agggacctcg tgccgaattc   2940
ctgcagcccg ggggatcc                                                 2958
```

<210> SEQ ID NO 6
<211> LENGTH: 4147
<212> TYPE: DNA
<213> ORGANISM: Artificial Sequence
<220> FEATURE:
<223> OTHER INFORMATION: Description of Artificial Sequence: Clone KIAA1092 (Genbank ID AB029015)

<400> SEQUENCE: 6

```
ccgcgcgcgg cggcccgagg cggcggcggg gacgcgggga cgcgaggacg cggctttgtg     60
caggcgggtc gcggggcgcc catggcggag tgcggccggg ggggcgccgc cggcggggcc    120
ctgcccacct ccccgggccc ggccctcggc gccaagggcg ccctgaaagc cggagtgggg    180
gaaggcggtg gcgggggagg tcgcctcggc cacgggcggg cgcgctatga cagcggcggg    240
gtttccaacg gagactgcag cctcggcgtg tccggggacg aagcccgggc tagccctacc    300
aggggacccc gcggcgttgc gctcgccccg acccccagcg cggtcgtctg taccctcccc    360
cgggagagca agccgggcgg cctgccccgc cggagcagca tcatcaagga tggtacaaaa    420
cagaagaggg aacggaaaaa gacagtctca ttcagcagca tgccaacaga gaagaagatc    480
agcagtgcaa gtgattgtat taattcaatg gttgagggtt cagaactcaa aaaggttcgc    540
tccaactcta gaatttatca taggtacttt ttactggatg ctgacatgca gagcctaagg    600
tgggagccat ctaagaagga ttctgagaaa gccaagattg acattaaatc catcaaggaa    660
gtgagaacag gaaaaaacac agacatattc cgcagcaatg gcatttctga ccagatatct    720
gaagattgtg cgttttccgt catatatgga gagaattatg agtcactgga tttggttgcc    780
aactccgcag atgttgcaaa catctgggtt acaggactgc ggtacctaat ttcttatgga    840
aaacatacac ttgatatgtt agaaagtagc caagataaca tgaggacttc ttgggtttca    900
caaatgttta gtgaaattga tgtagataac cttggacata taactctgtg taatgctgtg    960
caatgtatca gaaacctcaa tcctggttta aaaacgagca aaattgagct taagttcaaa   1020
gaattgcata aatcaaagga caaagctggt accgaggtca caaaggaaga atttattgag   1080
```

-continued

```
gtttttcatg agctttgtac tagacctgaa atttatttcc ttttagttca gttttcaagc   1140
aataaagaat tccttgatac caaggacctt atgatgtttc ttgaggcaga acagggtgtg   1200
gcacatataa atgaggaaat aagccttgaa attattcaca aatatgaacc atccaaagag   1260
ggtcaggaaa agggctggct ctccatagac gggttcacta attaccttat gtcacctgac   1320
tgttatatat tcgatccaga acataagaag gtctgtcagg atatgaagca acctctgtct   1380
cattacttta taaactcatc tcataataca tacttaatag aggatcagtt ccgaggtccc   1440
tccgacatca caggatatat tcgagctctt aaaatgggtt gccggagtgt tgaattagat   1500
gtatgggatg ggccggacaa tgaacctgta atttacacag gccacaccat gacctctcag   1560
atagttttcc gcagtgtcat tgatattatt aacaagtatg cattctttgc ttcagagtat   1620
cctcttatct tgtgtttaga aaaccactgt tccattaaac aacagaaggt aatggttcag   1680
cacatgaaga aacttttagg agacaagctc tatacaacat cacccaatgt tgaggaatct   1740
tatctaccat ccccagatgt cctgaaaggg aaaatactaa ttaaagcaaa gaagctgtcc   1800
tcaaattgct ctggggtaga aggagatgtt actgacgaag atgaaggagc agaaatgtct   1860
cagaggatgg gaaaagagaa catggagcaa cccaataatg tgcctgtgaa gcgatttcag   1920
ctttgtaaag aactgtctga actggtcagc atctgcaaat cagttcagtt caaagaattt   1980
caggtgtcgt ttcaggttca gaagtactgg gaagtctgtt cctttaatga agtgcttgcc   2040
agcaagtacg ccaatgaaaa tccaggggac tttgtaaatt acaacaaacg ttttcttgct   2100
agggtttttc ccagtccaat gagaattgat tccagtaaca tgaatcctca agatttttgg   2160
aaatgtggtt gccaaattgt agccatgaac tttcagacac caggactgat gatggacctg   2220
aatattggct ggtttaggca gaacggaaac tgtggctatg tcctccggcc agccatcatg   2280
agggaggagg tctccttctt cagcgccaat acaaaagact ctgtcccagg ggtctcacct   2340
caacttcttc acattaaaat catcagtggg cagaactttc ccaagcccaa aggatcaggt   2400
gccaaaggtg atgtggtaga tccttatgtc tatgttgaaa tccatggaat ccctgctgat   2460
tgtgcagaac aaaggacaaa aacagtgcac cagaatggag acgctcccat ttttgatgaa   2520
agctttgaat ttcaaatcaa cctgcctgaa ctggccatgg tgcgctttgt agtgctggat   2580
gatgactaca ttggggatga attcatcggc cagtacacaa ttccctttga atgtttacag   2640
acgggctacc gccatgtccc cctgcagtcc ttaactggag aggtccttgc acatgcttct   2700
ttatttgtcc acgtggctat tactaaccga agaggaggag gaaagcctca taaaaggggc   2760
ctttctgtga gaaaagggaa gaaatccagg gaatatgcat ctttgagaac actgtggatt   2820
aaaaccgtgg atgaggtatt caagaatgcc cagcccccta tacgggatgc cacagatctg   2880
agagaaaaca tgcagaatgc ggtggtgtca ttcaaggagc tgtgtggcct ctcctctgtg   2940
gccaatctca tgcagtgcat gttggcggtg tctccccgct ttctggggcc cgataacaca   3000
cccctagtgg tcctaaatct cagcgagcag taccccacaa tggagctgca gggaattgtg   3060
ccggaggttc tgaagaagat cgtaacaact tatgacatga tgattcagtc cctcaaggcg   3120
ttgattgaaa atgcagatgc tgtatatgaa aagatcgtac attgtcagaa ggcagccatg   3180
gaattccatg aacacttgca cagcataggc accaaggaag gtttgaagga aagaaaacta   3240
caaaaagcag tggagagctt tacctggaat attaccatct taaagggaca agcagatctt   3300
ttgaaatatg ctaagaatga gacattggag aacctgaaac aaatccattt tgctgctgtt   3360
tcatgtggac tgaataaacc aggcaccgaa aatgctgatg tccagaagcc acgccggagc   3420
```

-continued

```
ttggaagtca tacccgaaaa agcaaacgat gaaactggag aatgaggaaa cttacaataa   3480

accattatgg agtttataac tctaggacca attgtagtca gatgggacat ttgctttgca   3540

ctcactaatg agaataatat tcgggatttt aaagcacaac tggaatagct aattacagtc   3600

tattaaaact gtgaatgtat gtagcaatcc tgcgtgtgaa ggcaaataaa ctctttaaca   3660

ggcaattata ttgctggcca aaatatgcta tatttgtata caaagacatt ctaactcagt   3720

tccagtatga agaaagatta ttcactctag ctccactgag aaacattttc ctaagtgaaa   3780

acaatttctt aagatggaaa tggattggat tgtcaaatta ttatttattg gagaaaaaaa   3840

cctgatctac acatttttac ttatatgggg ttgccagagt ctctgggttc tagatgattt   3900

tggtggcatg cttgctgagc cataattact aaagagaatg taagtggacg ggttccctga   3960

atccccgggg tccttggaga gccatcgagg agaatgtgca attggactga agctccctgg   4020

ctgaagatac atgccgagtc agcacatggg tagagatgat gtaaaagcag ccaatctgga   4080

aacaatacat tgtaaatagt ttttcattgt atgaagtagt gttcacatta aaaagatgtt   4140

ttatgat                                                             4147
```

<210> SEQ ID NO 7
<211> LENGTH: 1154
<212> TYPE: PRT
<213> ORGANISM: Artificial Sequence
<220> FEATURE:
<223> OTHER INFORMATION: Description of Artificial Sequence: Clone KIAA1092 (Genbank ID AB029015)

<400> SEQUENCE: 7

```
Pro Arg Ala Ala Ala Arg Gly Gly Gly Gly Asp Ala Gly Thr Arg Gly
  1               5                  10                  15

Arg Gly Phe Val Gln Ala Gly Arg Gly Ala Pro Met Ala Glu Cys Gly
             20                  25                  30

Arg Gly Gly Ala Ala Gly Gly Ala Leu Pro Thr Ser Pro Gly Pro Ala
         35                  40                  45

Leu Gly Ala Lys Gly Ala Leu Lys Ala Gly Val Gly Glu Gly Gly Gly
     50                  55                  60

Gly Gly Gly Arg Leu Gly His Gly Arg Ala Arg Tyr Asp Ser Gly Gly
 65                  70                  75                  80

Val Ser Asn Gly Asp Cys Ser Leu Gly Val Ser Gly Asp Glu Ala Arg
                 85                  90                  95

Ala Ser Pro Thr Arg Gly Pro Arg Gly Val Ala Leu Ala Pro Thr Pro
            100                 105                 110

Ser Ala Val Val Cys Thr Leu Pro Arg Glu Ser Lys Pro Gly Gly Leu
        115                 120                 125

Pro Arg Arg Ser Ser Ile Ile Lys Asp Gly Thr Lys Gln Lys Arg Glu
    130                 135                 140

Arg Lys Lys Thr Val Ser Phe Ser Ser Met Pro Thr Glu Lys Lys Ile
145                 150                 155                 160

Ser Ser Ala Ser Asp Cys Ile Asn Ser Met Val Glu Gly Ser Glu Leu
                165                 170                 175

Lys Lys Val Arg Ser Asn Ser Arg Ile Tyr His Arg Tyr Phe Leu Leu
            180                 185                 190

Asp Ala Asp Met Gln Ser Leu Arg Trp Glu Pro Ser Lys Lys Asp Ser
        195                 200                 205

Glu Lys Ala Lys Ile Asp Ile Lys Ser Ile Lys Glu Val Arg Thr Gly
    210                 215                 220
```

-continued

```
Lys Asn Thr Asp Ile Phe Arg Ser Asn Gly Ile Ser Asp Gln Ile Ser
225                 230                 235                 240

Glu Asp Cys Ala Phe Ser Val Ile Tyr Gly Glu Asn Tyr Glu Ser Leu
                245                 250                 255

Asp Leu Val Ala Asn Ser Ala Asp Val Ala Asn Ile Trp Val Thr Gly
            260                 265                 270

Leu Arg Tyr Leu Ile Ser Tyr Gly Lys His Thr Leu Asp Met Leu Glu
        275                 280                 285

Ser Ser Gln Asp Asn Met Arg Thr Ser Trp Val Ser Gln Met Phe Ser
    290                 295                 300

Glu Ile Asp Val Asp Asn Leu Gly His Ile Thr Leu Cys Asn Ala Val
305                 310                 315                 320

Gln Cys Ile Arg Asn Leu Asn Pro Gly Leu Lys Thr Ser Lys Ile Glu
                325                 330                 335

Leu Lys Phe Lys Glu Leu His Lys Ser Lys Asp Lys Ala Gly Thr Glu
            340                 345                 350

Val Thr Lys Glu Glu Phe Ile Glu Val Phe His Glu Leu Cys Thr Arg
        355                 360                 365

Pro Glu Ile Tyr Phe Leu Leu Val Gln Phe Ser Ser Asn Lys Glu Phe
    370                 375                 380

Leu Asp Thr Lys Asp Leu Met Met Phe Leu Glu Ala Glu Gln Gly Val
385                 390                 395                 400

Ala His Ile Asn Glu Glu Ile Ser Leu Glu Ile Ile His Lys Tyr Glu
                405                 410                 415

Pro Ser Lys Glu Gly Gln Glu Lys Gly Trp Leu Ser Ile Asp Gly Phe
            420                 425                 430

Thr Asn Tyr Leu Met Ser Pro Asp Cys Tyr Ile Phe Asp Pro Glu His
        435                 440                 445

Lys Lys Val Cys Gln Asp Met Lys Gln Pro Leu Ser His Tyr Phe Ile
    450                 455                 460

Asn Ser Ser His Asn Thr Tyr Leu Ile Glu Asp Gln Phe Arg Gly Pro
465                 470                 475                 480

Ser Asp Ile Thr Gly Tyr Ile Arg Ala Leu Lys Met Gly Cys Arg Ser
                485                 490                 495

Val Glu Leu Asp Val Trp Asp Gly Pro Asp Asn Glu Pro Val Ile Tyr
            500                 505                 510

Thr Gly His Thr Met Thr Ser Gln Ile Val Phe Arg Ser Val Ile Asp
        515                 520                 525

Ile Ile Asn Lys Tyr Ala Phe Phe Ala Ser Glu Tyr Pro Leu Ile Leu
    530                 535                 540

Cys Leu Glu Asn His Cys Ser Ile Lys Gln Gln Lys Val Met Val Gln
545                 550                 555                 560

His Met Lys Lys Leu Leu Gly Asp Lys Leu Tyr Thr Thr Ser Pro Asn
                565                 570                 575

Val Glu Glu Ser Tyr Leu Pro Ser Pro Asp Val Leu Lys Gly Lys Ile
            580                 585                 590

Leu Ile Lys Ala Lys Lys Leu Ser Ser Asn Cys Ser Gly Val Glu Gly
        595                 600                 605

Asp Val Thr Asp Glu Asp Glu Gly Ala Glu Met Ser Gln Arg Met Gly
    610                 615                 620

Lys Glu Asn Met Glu Gln Pro Asn Asn Val Pro Val Lys Arg Phe Gln
625                 630                 635                 640

Leu Cys Lys Glu Leu Ser Glu Leu Val Ser Ile Cys Lys Ser Val Gln
```

-continued

```
                645                 650                 655

Phe Lys Glu Phe Gln Val Ser Phe Gln Val Gln Lys Tyr Trp Glu Val
            660                 665                 670

Cys Ser Phe Asn Glu Val Leu Ala Ser Lys Tyr Ala Asn Glu Asn Pro
        675                 680                 685

Gly Asp Phe Val Asn Tyr Asn Lys Arg Phe Leu Ala Arg Val Phe Pro
    690                 695                 700

Ser Pro Met Arg Ile Asp Ser Ser Asn Met Asn Pro Gln Asp Phe Trp
705                 710                 715                 720

Lys Cys Gly Cys Gln Ile Val Ala Met Asn Phe Gln Thr Pro Gly Leu
                725                 730                 735

Met Met Asp Leu Asn Ile Gly Trp Phe Arg Gln Asn Gly Asn Cys Gly
            740                 745                 750

Tyr Val Leu Arg Pro Ala Ile Met Arg Glu Glu Val Ser Phe Phe Ser
        755                 760                 765

Ala Asn Thr Lys Asp Ser Val Pro Gly Val Ser Pro Gln Leu Leu His
    770                 775                 780

Ile Lys Ile Ile Ser Gly Gln Asn Phe Pro Lys Pro Lys Gly Ser Gly
785                 790                 795                 800

Ala Lys Gly Asp Val Val Asp Pro Tyr Val Tyr Val Glu Ile His Gly
                805                 810                 815

Ile Pro Ala Asp Cys Ala Glu Gln Arg Thr Lys Thr Val His Gln Asn
            820                 825                 830

Gly Asp Ala Pro Ile Phe Asp Glu Ser Phe Glu Phe Gln Ile Asn Leu
        835                 840                 845

Pro Glu Leu Ala Met Val Arg Phe Val Val Leu Asp Asp Asp Tyr Ile
    850                 855                 860

Gly Asp Glu Phe Ile Gly Gln Tyr Thr Ile Pro Phe Glu Cys Leu Gln
865                 870                 875                 880

Thr Gly Tyr Arg His Val Pro Leu Gln Ser Leu Thr Gly Glu Val Leu
                885                 890                 895

Ala His Ala Ser Leu Phe Val His Val Ala Ile Thr Asn Arg Arg Gly
            900                 905                 910

Gly Gly Lys Pro His Lys Arg Gly Leu Ser Val Arg Lys Gly Lys Lys
        915                 920                 925

Ser Arg Glu Tyr Ala Ser Leu Arg Thr Leu Trp Ile Lys Thr Val Asp
    930                 935                 940

Glu Val Phe Lys Asn Ala Gln Pro Pro Ile Arg Asp Ala Thr Asp Leu
945                 950                 955                 960

Arg Glu Asn Met Gln Asn Ala Val Val Ser Phe Lys Glu Leu Cys Gly
                965                 970                 975

Leu Ser Ser Val Ala Asn Leu Met Gln Cys Met Leu Ala Val Ser Pro
            980                 985                 990

Arg Phe Leu Gly Pro Asp Asn Thr Pro Leu Val Val Leu Asn Leu Ser
        995                 1000                1005

Glu Gln Tyr Pro Thr Met Glu Leu Gln Gly Ile Val Pro Glu Val Leu
    1010                1015                1020

Lys Lys Ile Val Thr Thr Tyr Asp Met Met Ile Gln Ser Leu Lys Ala
1025                1030                1035                1040

Leu Ile Glu Asn Ala Asp Ala Val Tyr Glu Lys Ile Val His Cys Gln
                1045                1050                1055

Lys Ala Ala Met Glu Phe His Glu His Leu His Ser Ile Gly Thr Lys
            1060                1065                1070
```

-continued

Glu Gly Leu Lys Glu Arg Lys Leu Gln Lys Ala Val Glu Ser Phe Thr
1075 1080 1085

Trp Asn Ile Thr Ile Leu Lys Gly Gln Ala Asp Leu Leu Lys Tyr Ala
1090 1095 1100

Lys Asn Glu Thr Leu Glu Asn Leu Lys Gln Ile His Phe Ala Ala Val
1105 1110 1115 1120

Ser Cys Gly Leu Asn Lys Pro Gly Thr Glu Asn Ala Asp Val Gln Lys
1125 1130 1135

Pro Arg Arg Ser Leu Glu Val Ile Pro Glu Lys Ala Asn Asp Glu Thr
1140 1145 1150

Gly Glu

<210> SEQ ID NO 8
<211> LENGTH: 3238
<212> TYPE: DNA
<213> ORGANISM: Homo sapiens

<400> SEQUENCE: 8
caggtggaaa aagacagtct cattcagcag catgccaaca gagaagaaga tcagcagtgc 60
aagtgattgt attaattcaa tggttgaggg ttcagaactc aaaaaggttc gctccaactc 120
tagaatttat cataggtact ttctactgga tgctgacatg cagagcctaa ggtgggagcc 180
atctaagaag gattctgaga aagccaagat tgacattaaa tccatcaagg aagtgagaac 240
gggaaaaaac acagacatat tccgcagcaa tggcatttct gaccagatat ctgaagattg 300
tgcgttttcc gtcatatatg gagagaatta tgagtcactg gatttggttg ccactctcgc 360
agatgttgca aacatctggg ttacaggact gcggtaccta atttcttatg gaaaacatac 420
acttgatatg ttagaaagta gccaagataa catgaggact tcttgggttt cacaaatgtt 480
tagtgaaatt gatgtagata accttggaca tataactctg tgtaatgctg tgcaatgtat 540
cagaaacctc aatcctggtt taaaaacgag caaaattgag cttaagttca aagaattgca 600
taaatcaaag gacaaagctg gtaccgaggt cacaaaggaa gaatttattg aggtttttca 660
tgagctttgt actagacctg aaatttattt cctttttagtt cagttttcaa gcaataaaga 720
attccttgat accaaggacc ttatgatgtt tcttgaggca gaacagggtg tggcacatat 780
aaatgaggaa ataagccttg aaattattca caaatatgaa ccatccaaag agggtcagga 840
aaagggctgg ctctccatag acgggttcac taattacctt atgtcacctg actgttatat 900
attcgatcca gaacataaga aggtctgtca ggatatgaag caacctctgt ctcattactt 960
tataaactca tctcataata catacttaat agaggatcag ttccgaggtc cctccgacat 1020
cacaggatat attcgagctc ttaaaatggg ttgccggagt gttgaattag atgtatggga 1080
tgggccggac aatgaacctg taatttacac aggccacacc atgacctctc agatagtttt 1140
ccgcagtgtc attgatatta ttaacaagta tgcattcttt gcttcagagt atcctcttat 1200
cttgtgttta gaaaaccact gttccattaa acaacagaag gtaatggttc agcacatgaa 1260
gaaactttta ggagacaagc tctatacaac atcacccaat gttgaggaat cttatctacc 1320
atccccagat gtcctgaaag ggaaaatact aattaaagca aagaagctgt cctcaaattg 1380
ttctggggta gaaggagatg ttactgacga agatgaagga gcagaaatgt ctcagaggat 1440
gggaaaagag aacatggagc aacccaataa tgtgcctgtg aagcgatttc agctttgtaa 1500
agaactgtct gaactggtca gcatctgcaa atcagttcag ttcaaagaat ttcaggtgtc 1560
gtttcaggtt cagaagtact gggaagtctg ttcctttaat gaagtgcttg ccagcaagta 1620

-continued cgccaatgaa aatccagggg actttgtaaa ttacaacaaa cgttttcttg ctagggtttt 1680
tcccagtcca atgagaattg attccagtaa catgaatcct caagattttt ggaaatgtgg 1740
ttgccaaatt gtagccatga actttcagac accaggactg atgatggacc tgaatattgg 1800
ctggtttagg cagaacggaa actgtggcta tgtcctccgg ccagccatca tgagggagga 1860
ggtctccttc ttcagcgcca atacaaaaga ctctgtccca ggggtctcac ctcaacttct 1920
tcacattaaa atcatcagtg ggcagaactt tcccaagccc aaaggatcag gtgccaaagg 1980
tgatgtggta gatccttatg tctatgttga aatccatgga atccctgctg attgtgcaga 2040
acaaaggaca aaaacagtgc accagaatgg agacgctccc atttttgatg aaagctttga 2100
atttcaaatc aacctgcctg aactggccat ggtgcgcttt gtagtgctgg atgatgacta 2160
cattggggat gaattcatgg gccagtacac aattcccttt gaatgtttac agacgggcta 2220
ccgccatgtc cccctgcagt ccttaactgg agaggtcctt gcacatgctt ctttatttgt 2280
ccacgtggct attactaacc gaagagtagg aggaaagcct cataaaaggg gcctttctgt 2340
gagaaaaggg aagaaatcca gggaatatgc atctttgaga acactgtgga ttaaaaccgt 2400
ggatgaggta ttcaagaatg cccagccccc tatacgggat gccacagatc tgagagaaaa 2460
catgcagaat gcggtggtgt cattcaagga gctgtgtggc ctctcctctg tggccaatct 2520
catgcagtgc atgttggcgg tgtctccccg ctttctgggg cccgataaca cacccctagt 2580
ggtcctaaat ctcagcgagc agtaccccac aatggagctg cagggaattg tgtcggaggt 2640
tctgaagaag atcgtaacaa cttatgacat gatgattcag tccctcaagg cgttgattga 2700
aaatgcagat gctgtatatg aaaagatcgt acattgtcag aaggcagcca tggaattcca 2760
tgaacacttg cacagcatag gcaccaagga aggtttgaag gaaagaaaac tacaaaaagc 2820
agtggagagc tttacctgga atattaccat cttaaaggga caagcagatc ttttgaaata 2880
tgctaagaat gagacattgg agaacctgaa acaaatccat tttgctgctg tttcatgtgg 2940
actgaataaa ccaggcaccg aaaatgctga tgtccagaag ccacgccgga gcttggaagt 3000
catacccgaa aaagcaaacg atgaaactgg agaatgagga aacttacaat aaaccattat 3060
ggagtttata actctaggac caattgtagt cagatgggac atttgctttg cactcactaa 3120
tgagaataat attcgggatt ttaaagcaca actggaatag ctaattcagt ctttaaaact 3180
gggaatgtat gtagccaatc ctgcgtgtga aggcaaataa cttttttaac aggcaatt 3238

<210> SEQ ID NO 9
<211> LENGTH: 916
<212> TYPE: PRT
<213> ORGANISM: Rattus sp.

<400> SEQUENCE: 9

Met Pro Thr Glu Lys Lys Ile Ser Ser Ala Ser Asp Cys Ile Asn Ser
1 5 10 15

Met Val Glu Gly Ser Glu Leu Lys Lys Val Arg Ser Asn Ser Arg Ile
20 25 30

Tyr His Arg Tyr Phe Leu Leu Asp Ala Asp Met Gln Ser Leu Arg Trp
35 40 45

Glu Pro Ser Lys Lys Asp Ser Glu Lys Ala Lys Ile Asp Ile Lys Ser
50 55 60

Ile Lys Glu Val Arg Thr Gly Lys Asn Thr Asp Ile Phe Pro Gln Gln
65 70 75 80

Trp Ala Phe Leu Ser Lys Tyr Leu Lys Asp Cys Ala Phe Ser Val Ile

-continued

```
                85                  90                  95

Tyr Gly Glu Asn Met Ser His Ser Asp Leu Val Ala Asn Ser Ala Asp
            100                 105                 110

Val Ala Asn Ile Trp Val Thr Gly Leu Arg Tyr Leu Ile Ser Tyr Gly
        115                 120                 125

Lys His Thr Leu Asp Met Leu Glu Ser Ser Gln Asp Asn Met Arg Thr
    130                 135                 140

Cys Trp Val Ser Gln Met Phe Ser Glu Ile Asp Val Asp Asp Leu Gly
145                 150                 155                 160

His Ile Thr Leu Cys Asn Ala Val Gln Cys Ile Arg Asn Leu Asn Pro
                165                 170                 175

Gly Leu Lys Thr Ser Lys Ile Glu Leu Lys Phe Lys Glu Leu His Lys
            180                 185                 190

Ser Lys Asp Lys Thr Gly Thr Glu Ile Thr Lys Glu Glu Phe Val Glu
        195                 200                 205

Val Phe His Glu Leu Cys Thr Arg Pro Glu Ile Tyr Phe Leu Leu Val
    210                 215                 220

Gln Phe Ser Ser Asn Lys Glu Phe Leu Asp Thr Lys Asp Leu Met Met
225                 230                 235                 240

Phe Leu Glu Ala Glu Gln Gly Val Ala His Ile Asn Glu Glu Ile Ser
                245                 250                 255

Leu Glu Ile Ile His Lys Tyr Glu Pro Ser Lys Glu Gly Gln Glu Lys
            260                 265                 270

Gly Trp Leu Ser Ile Asp Gly Phe Thr Asn Tyr Leu Met Ser Pro Asp
        275                 280                 285

Cys Tyr Ile Phe Asp Pro Glu His Lys Lys Val Cys Gln Asp Met Lys
    290                 295                 300

Gln Pro Leu Ser His Tyr Phe Ile Asn Ser Ser His Asn Thr Tyr Leu
305                 310                 315                 320

Ile Glu Asp Gln Phe Pro Gly Pro Ser Asp Ile Thr Gly Tyr Ile Arg
                325                 330                 335

Ala Leu Lys Met Gly Cys Arg Ser Val Glu Leu Asp Val Trp Asp Gly
            340                 345                 350

Pro Asp Asn Glu Pro Val Ile Tyr Thr Gly His Thr Met Thr Ser Gln
        355                 360                 365

Ile Val Phe Arg Ser Val Ile Asp Ile Ile Asn Lys Tyr Ala Phe Phe
    370                 375                 380

Ala Ser Glu Tyr Pro Leu Ile Leu Cys Leu Glu Asn His Cys Ser Ile
385                 390                 395                 400

Lys Gln Gln Lys Val Met Val Gln His Met Lys Lys Ile Leu Gly Asp
                405                 410                 415

Lys Leu Tyr Thr Thr Ser Pro Asn Met Glu Glu Ser Tyr Leu Pro Ser
            420                 425                 430

Pro Asp Val Leu Lys Gly Lys Ile Leu Ile Lys Ala Lys Lys Leu Ser
        435                 440                 445

Ser Asn Cys Ser Gly Val Glu Gly Asp Val Thr Asp Glu Asp Glu Gly
    450                 455                 460

Ala Glu Met Ser Gln Arg Met Gly Lys Glu Asn Val Glu Gln Pro Asn
465                 470                 475                 480

His Val Pro Val Lys Arg Phe Gln Leu Cys Lys Asp Leu Ser Glu Leu
                485                 490                 495

Val Ser Ile Cys Lys Ser Val Gln Phe Lys Glu Phe Gln Val Ser Phe
            500                 505                 510
```

-continued

```
Gln Val Gln Lys Tyr Trp Glu Val Cys Ser Phe Asn Glu Val Leu Ala
        515                 520                 525

Ser Lys Tyr Ala Asn Glu Asn Pro Gly Asp Phe Val Asn Tyr Asn Lys
    530                 535                 540

Arg Phe Leu Ala Arg Val Phe Pro Ser Pro Met Arg Ile Asp Ser Ser
545                 550                 555                 560

Asn Met Asn Pro Gln Asp Phe Trp Lys Cys Gly Cys Gln Ile Val Ala
                565                 570                 575

Met Asn Phe Gln Thr Pro Gly Leu Met Met Asp Leu Asn Ile Gly Trp
            580                 585                 590

Phe Arg Gln Asn Gly Asn Trp Ala Leu Val Leu Arg Pro Ala Ile Met
        595                 600                 605

Arg Glu Glu Val Ser Phe Phe Ser Ala Asn Thr Lys Asp Ser Val Pro
    610                 615                 620

Gly Val Ser Pro Gln Leu Leu His Ile Lys Ile Ile Ser Gly Gln Asn
625                 630                 635                 640

Phe Pro Lys Pro Lys Gly Ser Gly Ala Lys Gly Asp Val Val Asp Pro
                645                 650                 655

Tyr Val Tyr Val Glu Ile His Gly Ile Pro Ala Asp Cys Ala Glu Gln
            660                 665                 670

Arg Thr Lys Thr Val Asn Gln Asn Gly Asp Ala Pro Met Phe Asp Glu
        675                 680                 685

Ser Phe Glu Phe Gln Ile Asn Leu Pro Glu Leu Ala Met Val Arg Phe
    690                 695                 700

Val Val Leu Asp Asp Asp Tyr Ile Gly Asp Glu Phe Ile Gly Gln Tyr
705                 710                 715                 720

Thr Ile Pro Phe Glu Cys Leu Gln Thr Gly Tyr Arg His Val Pro Leu
                725                 730                 735

Gln Ser Leu Thr Gly Glu Val Leu Ala His Ala Ser Leu Phe Val His
            740                 745                 750

Val Ala Ile Thr Asn Arg Arg Gly Gly Gly Lys Pro His Lys Arg Gly
        755                 760                 765

Leu Ser Val Arg Lys Gly Lys Lys Ser Arg Glu Tyr Ala Ser Leu Arg
    770                 775                 780

Thr Leu Trp Ile Lys Thr Val Asp Glu Val Phe Lys Asn Ala Gln Pro
785                 790                 795                 800

Pro Ile Arg Asp Ala Thr Asp Leu Arg Glu Asn Met Gln Asn Ala Val
                805                 810                 815

Val Ser Phe Lys Glu Leu Cys Gly Leu Ser Ser Val Ala Asn Leu Met
            820                 825                 830

Gln Cys Met Leu Ala Val Ser Pro Arg Phe Leu Gly Pro Asp Asn Thr
        835                 840                 845

Pro Leu Val Val Leu Asn Leu Ser Glu Pro Tyr Pro Thr Met Glu Leu
    850                 855                 860

Gln Ala Ile Val Pro Glu Val Leu Lys Lys Ile Val Thr Thr Tyr Asp
865                 870                 875                 880

Met Met Ile Gln Ser Leu Lys Ala Arg Leu Lys Met Gln Met Leu Cys
                885                 890                 895

Met Lys Arg Leu Cys Thr Val Arg Arg Gln Pro Trp Asn Phe Met Asn
            900                 905                 910

Thr Cys Thr Ala
        915
```

-continued

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: PH Domain primer 1

<400> SEQUENCE: 10
tattaattca atggttgag 19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: PH Domain primer 2

<400> SEQUENCE: 11
aagtgtatgt tttccataag 20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: EF-hand primer 1

<400> SEQUENCE: 12
agataacatg aggacttg 18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: EF-hand primer 2

<400> SEQUENCE: 13
acaaagctca tgaaaaacc 19

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: PLC X-region primer 1

<400> SEQUENCE: 14
agaacataag aaggtctgtc 20

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: PLC X-region primer 2

-continued

<400> SEQUENCE: 15
gtattttccc tttcagcag 19

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: PLC Y-region primer 1

<400> SEQUENCE: 16
gagaacatgg agcaaccc 18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: PLC Y-region primer 2

<400> SEQUENCE: 17
cctcatgatg gctggccgg 19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C2 domain primer 1

<400> SEQUENCE: 18
gagggaggag gtctccttc 19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: PCR primer
<220> FEATURE:
<223> OTHER INFORMATION: C2 domain primer 2

<400> SEQUENCE: 19
aattgtgtac tggcccatg 19

<210> SEQ ID NO 20
<211> LENGTH: 15
<212> TYPE: DNA
<213> ORGANISM: Artificial Sequence
<220> FEATURE:
<223> OTHER INFORMATION: Description of Artificial Sequence:
Oligonucleotide to be tested in cells for
antisense supporession of B-PLC function.

<400> SEQUENCE: 20
attgggttgc tccat 15

<210> SEQ ID NO 21
<211> LENGTH: 16
<212> TYPE: DNA

-continued

```
<213> ORGANISM: Artificial Sequence
<220> FEATURE:
<223> OTHER INFORMATION: Description of Artificial Sequence:
      Oligonucleotide to be tested in cells for
      antisense supporession of B-PLC function.

<400> SEQUENCE: 21

tagaaagtac ctatga                                                 16


<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:
      Phosphorothioate antisense oligonucleotide

<400> SEQUENCE: 22

aggattctca ttggcgtatt tactggctag cacttcattg                       40
```